(12) United States Patent
Dudzinski et al.

(10) Patent No.: US 11,189,376 B1
(45) Date of Patent: Nov. 30, 2021

(54) PATIENT TRACKING AND DYNAMIC UPDATING OF PATIENT PROFILE

(71) Applicant: West Corporation, Omaha, NE (US)

(72) Inventors: Robert J. Dudzinski, Omaha, NE (US); Jil M. Fisher, Omaha, NE (US); Troy G. Hottovy, Waterloo, NE (US); Pamela Ann Mortenson, Blair, NE (US); Craig A. Webster, Omaha, NE (US); Michelle Mason Winston, Omaha, NE (US)

(73) Assignee: INTRADO CORPORATION, Omaha, NE (US)

( * ) Notice: Subject to any disclaimer, the term of this patent is extended or adjusted under 35 U.S.C. 154(b) by 451 days.

(21) Appl. No.: 14/283,460

(22) Filed: May 21, 2014

(51) Int. Cl.
*G16H 40/20* (2018.01)
(52) U.S. Cl.
CPC .................. *G16H 40/20* (2018.01)
(58) Field of Classification Search
CPC ............ G06Q 50/22; G06Q 50/24; G06F 19/322–327; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00
See application file for complete search history.

(56) References Cited

U.S. PATENT DOCUMENTS

2002/0032583 A1* 3/2002 Joao ................. G16H 10/60
 705/2
2007/0276270 A1* 11/2007 Tran ................. A61B 5/002
 600/508

* cited by examiner

*Primary Examiner* — Reginald R Reyes

(57) ABSTRACT

Medical services are offered by various facilities near a patient's residence. The number of facility options continues to grow and the patients can now receive various different health care services. One example method of operation provides receiving sensor data indicating that one or more sensors were triggered at a predefined location at a first time during a monitoring event, receiving additional sensor data indicating an additional sensor was triggered at a second time later than the first time, identifying a time gap between the first time and the second time, storing the time gap in a schedule stored in memory, and creating a sensor trigger pattern based on the time gap and applying the sensor trigger pattern to an alert status for a subsequent monitoring event.

18 Claims, 27 Drawing Sheets

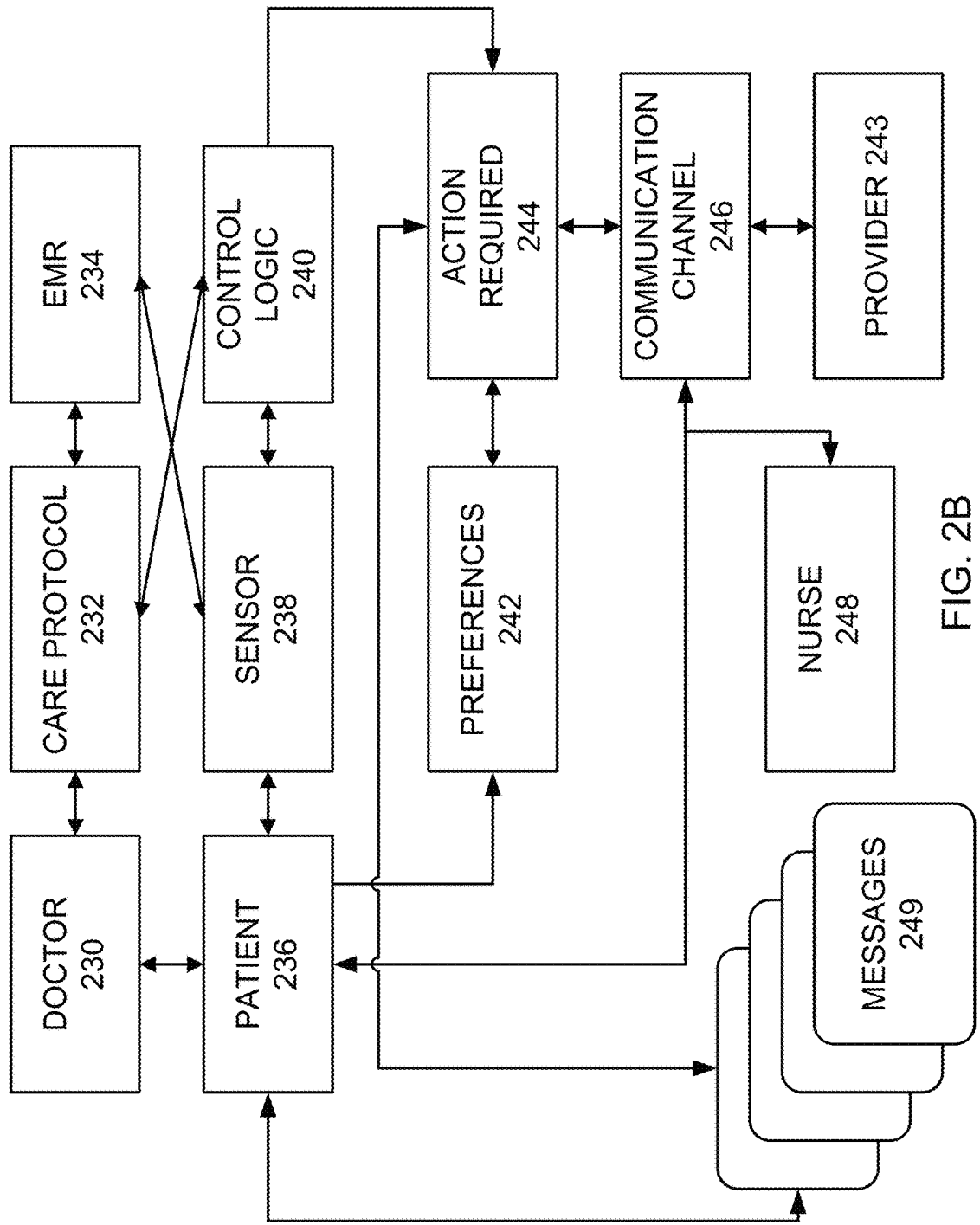

PATIENT TRACKING AND DYNAMIC UPDATING OF PATIENT PROFILE

CROSS-REFERENCE TO RELATED APPLICATIONS

This application incorporates by reference U.S. patent application Ser. No. 14/283,341; U.S. patent application Ser. No. 14/283,363; U.S. patent application Ser. No. 14/283,371; U.S. patent application Ser. No. 14/283,379; U.S. patent application Ser. No. 14/283,389; U.S. patent application Ser. No. 14/283,399; and U.S. patent application Ser. No. 14/283,405; each of which was filed on May 21, 2014, the entire contents of which are hereby incorporated by reference.

TECHNICAL FIELD OF THE APPLICATION

This application relates to assisting patients with continuing health care management via a computer-based application, and more specifically to optimizing patient information gathering, patient status updating, medical facility treatment and other aspects of medical patient interactions.

BACKGROUND OF THE APPLICATION

The majority of health care providers offer services, prescriptions, treatment regiments, advice, etc., to patients on a daily basis. As patients require access to doctors, prescription medicine, hospitals, etc., the number of options available for the patient may be numerous.

Health care facilities and services in place today in the United States usually rely on the individual patient or those caring for patient to decide when to visit the medical facility, which type of physician to call for an appointment, and to provide updated information pertaining to the patient's well-being or the present health concern being experienced by the patient.

SUMMARY OF THE APPLICATION

One example embodiment provides a method that includes receiving updated patient information at a patient profile server, identifying a patient medical profile stored in memory associated with the updated patient information, updating at least one patient status based on the updated patient information received, and modifying a patient schedule associated with the at least one patient status and storing the patient schedule in the patient medical profile.

Another example embodiment provides an apparatus that includes a receiver configured to receive updated patient information at a patient profile server, and a processor configured to identify a patient medical profile stored in memory associated with the updated patient information, update at least one patient status based on the updated patient information received, and modify a patient schedule associated with the at least one patient status and storing the patient schedule in the patient medical profile.

Another example embodiment provides a method that includes receiving at least one patient symptom at a patient monitoring server, calculating a medical professional selection score based on the at least one patient symptom, identifying a plurality of medical professionals having corresponding medical professional profiles based on the medical professional selection score, selecting a medical professional profile with the highest score, and transmitting a notification to the medical professional selected.

Yet another example embodiment provides an apparatus that includes a receiver configured to receive at least one patient symptom at a patient monitoring server, a processor configured to calculate a medical professional selection score based on the at least one patient symptom, identify a plurality of medical professionals having corresponding medical professional profiles based on the medical professional selection score, select a medical professional profile with the highest score, and a transmitter configured to transmit a notification to the medical professional selected.

Another example embodiment includes a method that includes receiving at least one patient symptom at a patient monitoring server, diagnosing the patient with at least one medical condition based on the at least one patient symptom, identifying a plurality of medical professionals having corresponding medical professional profiles that match the at least one medical condition, transmitting the at least one medical condition to a communication device of at least one of the medical professionals that is presently scheduled to be available, and receiving a response message indicating a course of action based on the medical condition.

Another example embodiment includes an apparatus that provides a receiver configured to receive at least one patient symptom at a patient monitoring server, a processor configured to diagnose the patient with at least one medical condition based on the at least one patient symptom, identify a plurality of medical professionals having corresponding medical professional profiles that match the at least one medical condition, and a transmitter configured to transmit the at least one medical condition to a communication device of at least one of the medical professionals that is presently scheduled to be available, and the receiver is further configured to receive a response message indicating a course of action based on the medical condition.

Another example embodiment includes a method that provides storing a plurality of user information parameters in a user profile of a user, identifying at least one future location status associated with the user profile of the user, requesting at least one data source provide updated location status information associated with the at least one future location, receiving the updated location status information, and comparing the updated location status information to the user information parameters to identify a match.

Another example embodiment includes an apparatus that includes a memory configured to store a plurality of user information parameters in a user profile of a user, a processor configured to identify at least one future location status associated with the user profile of the user, request at least one data source provide updated location status information associated with the at least one future location, and a receiver configured to receive the updated location status information, and wherein the processor is further configured to compare the updated location status information to the user information parameters to identify a match.

Another example embodiment may include a method that includes storing a plurality of user information parameters in a user profile of a user, identifying at least one future location status associated with the user profile of the user, identifying medical facilities within a predefined area of the at least one future location status, and initiating at least one medical action associated with at least one of the medical facilities and the user information parameters in the user profile.

Another example embodiment includes an apparatus that provides a memory configured to store a plurality of user information parameters in a user profile of a user, a processor configured to identify at least one future location status associated with the user profile of the user, identify medical facilities within a predefined area of the at least one future location status, and initiate at least one medical action associated with at least one of the medical facilities and the user information parameters in the user profile.

Still another example embodiment includes a method that provides retrieving a schedule associated with sensor data being received from a plurality of sensors, receiving updated sensor data from at least one of the plurality of sensors at an updated sensor data receive time, comparing the updated sensor data to the schedule, identifying a time discrepancy between the schedule and the updated sensor data receive time, and creating an alert status based on the discrepancy.

Still yet another example embodiment includes an apparatus that includes a processor configured to retrieve a schedule associated with sensor data being received from a plurality of sensors, a receiver configured to receive updated sensor data from at least one of the plurality of sensors at an updated sensor data receive time, and wherein the processor is further configured to compare the updated sensor data to the schedule, identify a time discrepancy between the schedule and the updated sensor data receive time, and create an alert status based on the discrepancy.

Still another example embodiment includes a method that provides receiving sensor data indicating that at least one sensor was triggered at a predefined location at a first time during a monitoring event, receiving additional sensor data indicating at least one additional sensor was triggered at a second time later than the first time, identifying a time gap between the first time and the second time, storing the time gap in a schedule stored in memory, and creating a sensor trigger pattern based on the time gap and applying the sensor trigger pattern to an alert status for a subsequent monitoring event.

Another example embodiment provides an apparatus that includes a receiver configured to receive sensor data indicating that at least one sensor was triggered at a predefined location at a first time during a monitoring event, and receive additional sensor data indicating at least one additional sensor was triggered at a second time later than the first time, and a processor configured to identify a time gap between the first time and the second time, and a memory configured to store the time gap in a schedule stored in memory, and the processor is further configured to create a sensor trigger pattern based on the time gap and applying the sensor trigger pattern to an alert status for a subsequent monitoring event.

Another example embodiment includes a method that provides retrieving a schedule associated with sensor data being received from a plurality of sensors, identifying a first sensor type set to trigger first before any other sensor being monitored during a first monitoring sequence, receiving an indication that the first sensor type has not triggered during the first monitoring sequence, identifying a second sensor type different from the first sensor type set to trigger at a later time than the first sensor type, and receiving an indication that the second sensor type has not triggered during the first monitoring sequence, and initiating a predefined time period prior to creating an alert.

Another example embodiment includes an apparatus that has a processor configured to retrieve a schedule associated with sensor data being received from a plurality of sensors, identify a first sensor type set to trigger first before any other sensor being monitored during a first monitoring sequence, and a receiver configured to receive an indication that the first sensor type has not triggered during the first monitoring sequence, and wherein the processor is also configured to identify a second sensor type different from the first sensor type set to trigger at a later time than the first sensor type, and the receiver is further configured to receive an indication that the second sensor type has not triggered during the first monitoring sequence, and the processor is further configured to initiate a predefined time period prior to creating an alert.

BRIEF DESCRIPTION OF THE DRAWINGS

FIG. 2B illustrates an example logic diagram of a patient tracking configuration, according to an example embodiment of the present application.

DETAILED DESCRIPTION OF THE INVENTION

It will be readily understood that the components of the present invention, as generally described and illustrated in the figures herein, may be arranged and designed in a wide variety of different configurations. Thus, the following detailed description of the embodiments of a method, apparatus, and system, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment of the present invention. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" has been used in the description of embodiments of the present invention, the invention may be applied to many types of network data, such as, packet, frame, datagram, etc. For purposes of this invention, the term "message" also includes packet, frame, datagram, and any equivalents thereof. Furthermore, while certain types of messages and signaling are depicted in exemplary embodiments of the invention, the invention is not limited to a certain type of message, and the invention is not limited to a certain type of signaling.

Figure 1:
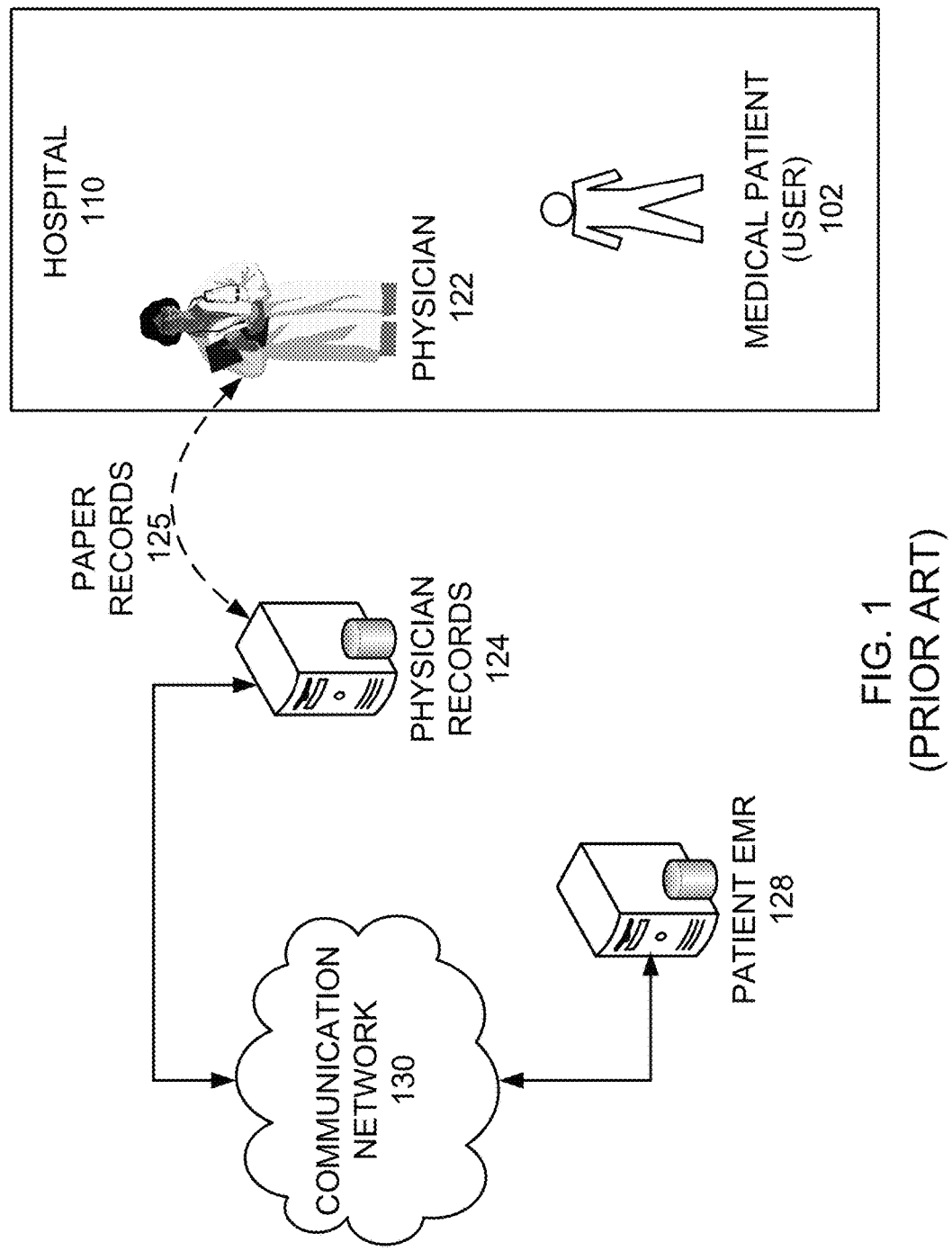
FIG. 1 illustrates a conventional prior art logic diagram of a user's interactions with a health care provider.

FIG. 1 illustrates a conventional prior art logic diagram of a network model of a user's interactions with a health care provider communication system. Referring to FIG. 1, the network configuration 100 would include a medical patient or user 102 communicating with a physician 122 via a live interaction at a hospital 110. The user 102 may be a patient that is presently undergoing treatment at the hospital 100 and who frequently interacts with a physician 122, who in turn may update a user medical record in a medical records database 124 via paper records 125. Alternatively, the records may be updated electronically via a wireless communication network and a computing device operated by the physician 122, however, regardless of the medium used to update the patient record, the records would still be updated manually via user interaction. Once the patient data is updated, the user's emergency medical record (EMR) may also be updated at a remote site 128 via a communication network 130.

Figure 2A:
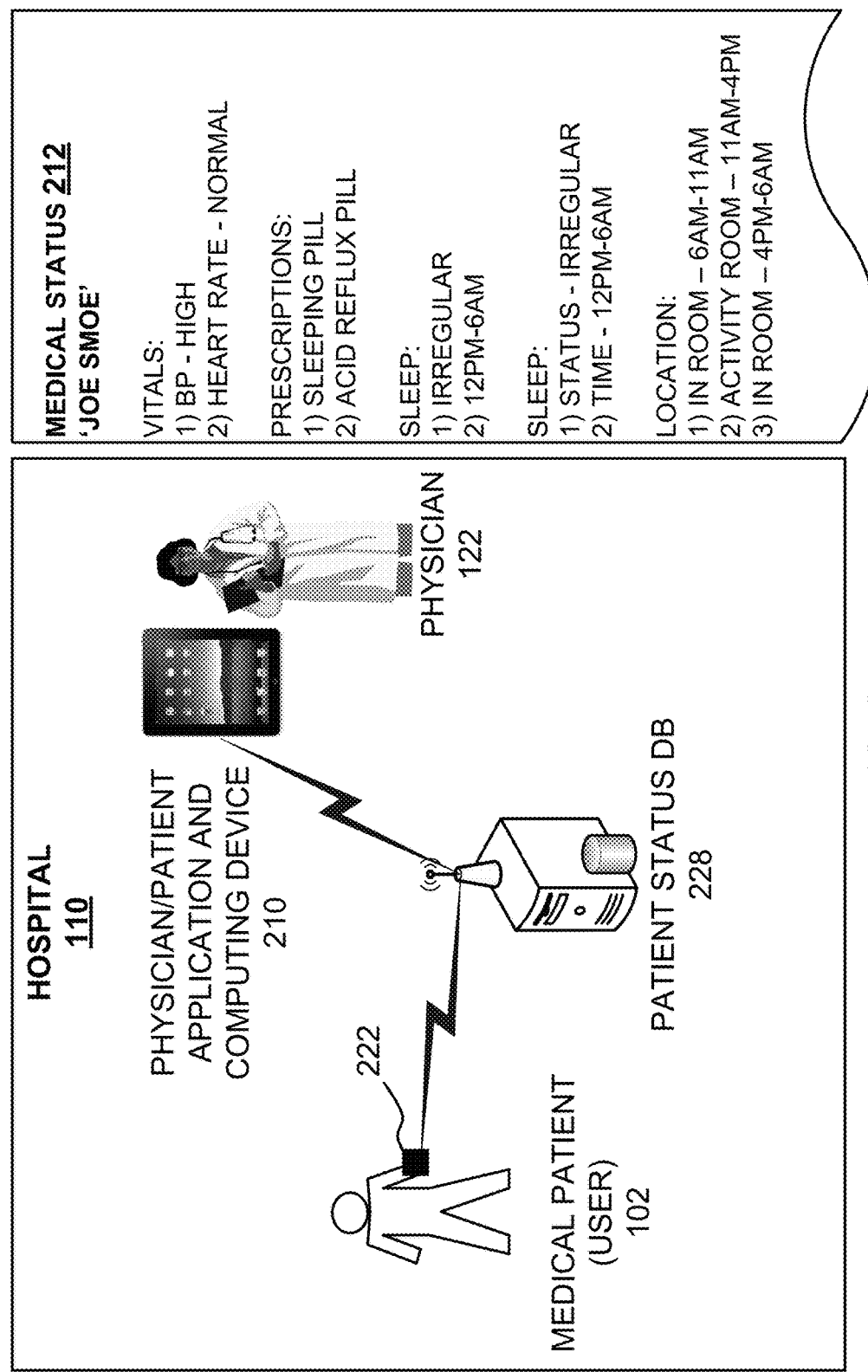
FIG. 2A illustrates an example network diagram of a patient tracking configuration, according to an example embodiment of the present application.

FIG. 2A illustrates an example logic diagram of a user's interactions with an automated patient monitoring application, according to an example embodiment of the present application. Referring to FIG. 2A, the network 200 includes a medical patient or user (hereinafter 'patient' and 'user' are used interchangeably throughout the disclosure). The user 102 may have a worn sensor 222 or may be exposed to various sensors/receivers/transmitters throughout the hospital room, floor, or greater hospital area to track a user's movement, status, condition, and/or other data related to the patient's status.

In operation, the user 102 may be wearing a tracking radio frequency (RF) device 122 to monitor location of the user 102. Alternatively, the user may be wearing a heart rate monitoring device, a blood pressure monitoring device, a blood sugar monitoring device, etc. that communicates with a patient status database 228. The patient's status may be updated periodically or based on a fixed schedule setup by the hospital or care facility. The physician 122 may receive updates based on the updated patient data to indicate a particular status change or a particular threshold that has been exceeded based on predetermined audit criteria.

The sensors 222 may be worn by the patient to identify movement, location and/or vitals. The sensors 222 may also be motion sensors, noise sensors, video sensors, etc. which are dispersed near the patient and in the patient's room, hallway, floor, etc. An example medical status 212 may be generated to identify the current status of the user. For example, the patient sensor data my indicate the patient's present vitals and may identify them as being nominal, low, high, dangerously high based on predetermined criteria. Also, the present prescriptions taken by the user are provided along with dosage. The sensors may offer other less commonly known data, such as the patient's sleep pattern and whether it is irregular, non-existent, nominal, more than usual, and may also include the times associated with the sleep patterns. Sleep patterns may be easily ascertained and generated based on the sensor data received. For example, if the user is moving around constantly at night, the sleep pattern may indicate a lack of sleep, while if the sensor remains motionless, the sleep pattern may be identified as being relatively constant. Also, a patient's location may be tracked for easy identification of when a patient should receive assistance or have his or her blood drawn, etc. These parameters can be used to automatically schedule meals, procedures and to identify whether the patient needs a sleep aid medication, different sleep arrangements, etc.

FIG. 2B illustrates an example of the data logic configuration used to perform the automated patient monitoring.

Referring to FIG. 2B, the logic diagram 250 illustrates a data and processing configuration that is used to perform patient monitoring and corresponding patient care plan updates, schedule modifications, prescription modifications, etc. In operation, the doctor 230 may be the named party to receive updates and in particular, status alerts that exceed a predetermined threshold. The care protocol 232 may represent the various thresholds for monitoring patient vitals, sleep patterns, location changes, prescriptions, etc. The emergency medical record 234 may be updated to reflect the requirements or changes to the patient's current care plan. The patient 236 is linked to the sensors 238, which are tracked periodically to receive data updates which are processed by control logic 240 to identify the patient's status. Additionally, user preferences 242 may be applied to results to assist with determining whether an action is required to modify a patient schedule, meal plan, prescription, procedure, etc. For example, the patient may have various desires, concerns, allergies, etc., which can be considered by the logic prior to making a decision to modify the patient's game plan. The action required 244 may be determined based on the sensor data 238, the preferences 242 and the predetermined criteria set by the doctor 230. The communication channel 246 may represent an action or automated control signal that is generated and transmitted to the appropriate server and to access the appropriate patient file to change the status and make the necessary changes to a patient's schedule. A nurse 248 may be notified for more common interactions which do not require a physician and the provider 243 may be notified for insurance purposes. In addition, data messages 249 may be generated to reflect the updates requiring approval by the physician or to inform the patient of the updates as a courtesy.

Figure 2C:
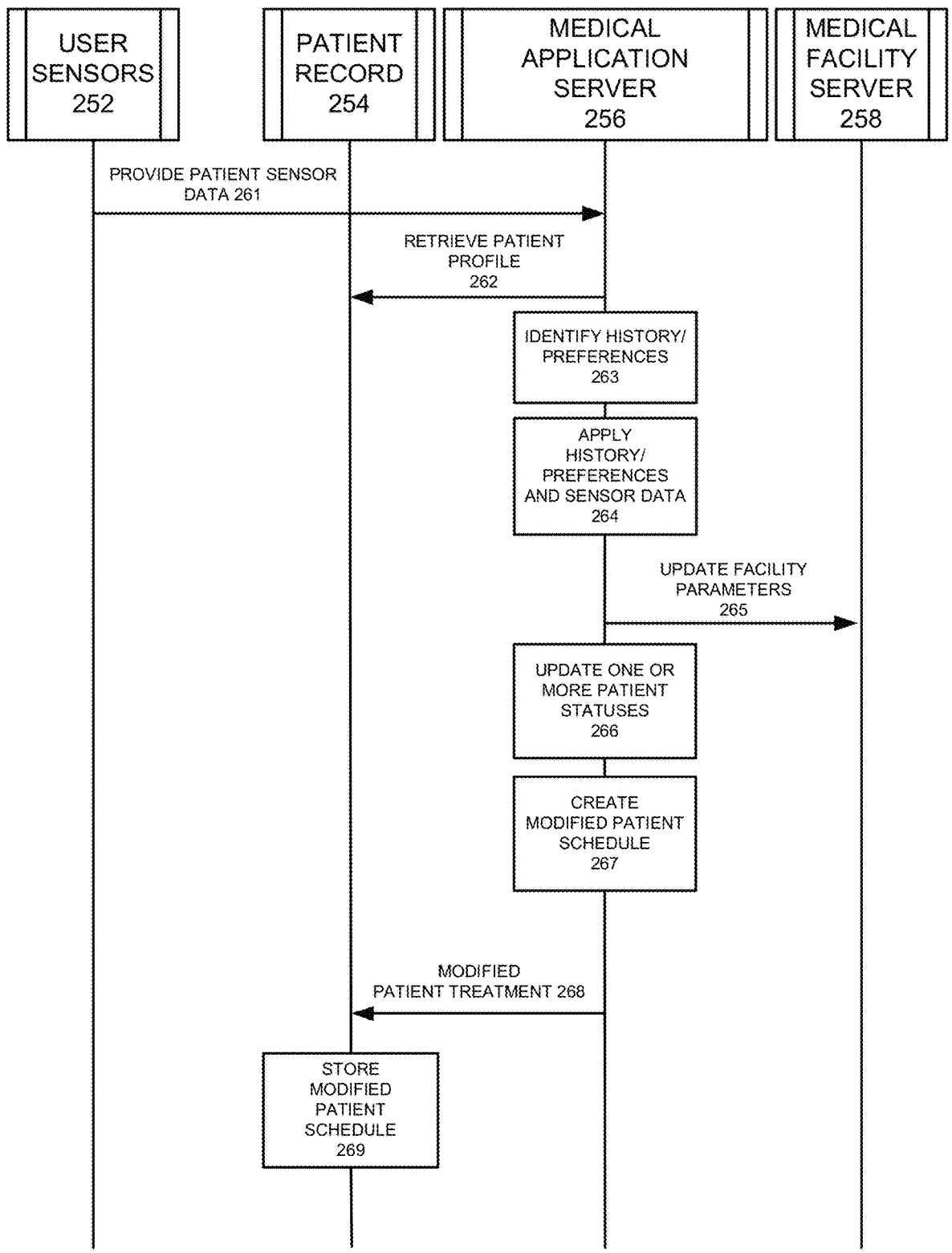
FIG. 2C illustrates an example system communication diagram of a patient tracking configuration, according to an example embodiment of the present application.

FIG. 2C illustrates an example system communication diagram of a patient sensor monitoring configuration according to example embodiments. Referring to FIG. 2C, the system 260 includes various user sensors 252 used to monitor patient activity and which are configured as transmission or trigger sensors. In one example, the sensors are RF sensors which transmit a data signal 261 to a receiver associated with a medical application server 256 configured to receive and store the patient sensor data. The data may be associated with a user patient record 254 which is retrieved 262 from memory and used to provide the basis for a determination as to whether any changes are required based on the received sensor data.

The patient profile may be used to identify whether the history information or user preferences 263 justify any changes to the user's present schedule or medical treatment plan. The patient history and preferences may be applied to the treatment plan to make any changes based on the sensor data 264. For example, the patient may have certain dietary requests, sleep requests, treatment requests and the sensor data may indicate that a change in the user's current treatment plan is necessary. The changes made are transmitted to a medical facility sever 258 via a facility parameter update message 265. The facility can then setup the future treatment accordingly based on the changes. The patient status may in turn be updated 266 and the modified patient schedule 267 is created and stored in the patient record 265 via a modified patient treatment message 268. The modified patient schedule 269 is stored in the patient record 254 and can be accessed for subsequent treatment efforts and updates based on future sensor data received.

One example method of operation may include receiving updated patient information at a patient profile server, which may be based on periodic patient sensor data received. The method may also include identifying a patient medical profile stored in memory associated with the updated patient information so the updated data can be stored in the patient record. The patient status can be updated based on the updated patient information received (i.e., sensor data), and a patient schedule can be modified to reflect the patient status change. All changes are stored in the patient schedule of the patient medical profile. Examples of the updated patient information may include patient consciousness, patient unconsciousness, patient location, patient eating status, patient vital sign status, patient moving status.

Each of the patient status indicators may be based on sensor data received. For example, the updated patient information is generated via at least one of a location sensor, a movement sensor, a patient vital sign measurement sensor and user submitted preference information. In operation, the plurality of updated patient information messages may be received over an interval of time, and a patient behavioral pattern may be identified as being associated with the updated patient information messages (i.e., abnormal sleep pattern, frequent movement throughout the facility, not eating scheduled meals, etc.). As a result, a current scheduled activity within the patient schedule may be modified based on the patient behavioral pattern. The current scheduled activity may be a patient meal delivery, a patient medication being administered, a patient blood drawing session, and a patient interface session. Additionally, a number of patient preferences may be retrieved from memory and applied to the schedule and/or procedure changing decision. Examples of the patient preferences include but are not limited to a meal preference, a sleep schedule, an entertainment preference, and a medication administering time, a procedure time, etc.

Figure 3A:
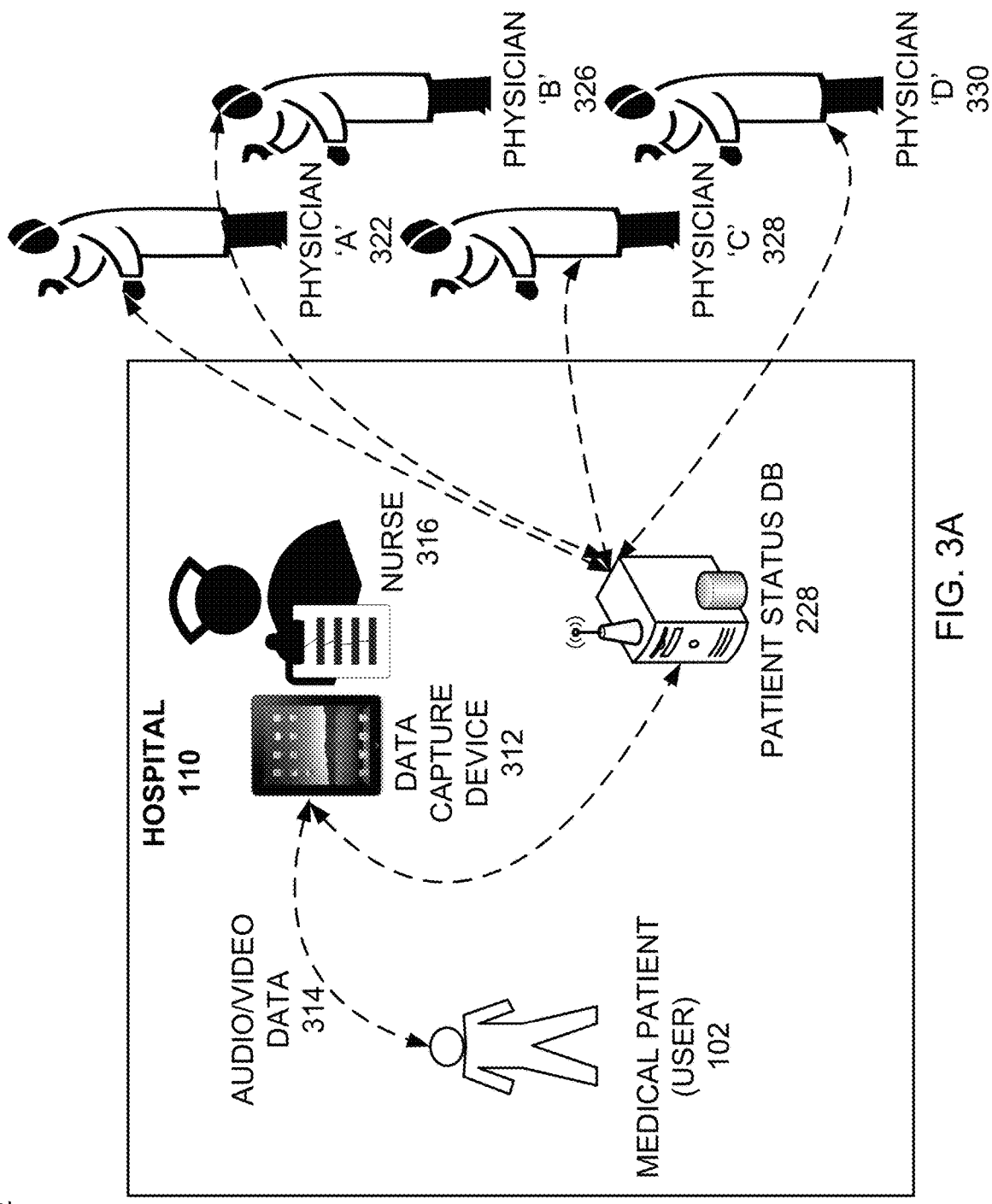
FIG. 3A illustrates an example network diagram of a patient and physician assignment configuration, according to an example embodiment of the present application.

FIG. 3A illustrates an example network diagram of a patient and physician assignment configuration, according to an example embodiment of the present application. In this embodiment, a medical patient or user 102 may be admitted to a hospital 110 and have his or her patient record accessed and updated to indicate the admission of the patent along with the patient's current status, symptoms, preferences, allergies, personal information, insurance, etc. During the admission or interfacing process, the patient 102 may be subject to a question and answer session with a staff member, such as a nurse 316, who may provide a preliminary analysis of the patient 102, and may capture audio and/or video information 314 via a hand held data capture device 312 (e.g., smartphone, camera, tablet, laptop, personal computer, etc.).

In operation, the patient's physical status may be captured via writing, video, audio, etc. and stored as a patient symptom(s) in a patient medical profile. The data capture device 312 is in communication with a patient status database (DB) 228 which receives the patient's symptom information along with other types of information and processes the data to determine which physician(s) are eligible to assist the patient depending on a variety of different factors. For example, factors may include the physician availability status, the physician on-call, the specialty of the physician, the patient's medical insurance policies, the recent patient symptoms, the updated patient symptoms, etc. As a result, various different physicians 322, 326, 328 and 330 may be part of a pool of potential candidates to provide immediate feedback, diagnosis, suggestions, courses of action, treatment plans, referrals, medication, etc. One physician may be on-call and the other physicians may be available at a later time. One physician may be general practice and the others may be the same or different types of specialists.

One example may include an initial status of the patient 102 having a bizarre rash identified by video and images and shared via the nurse 316 with a remote on-call physician 322. The physician 'A' 322 may be a general practice doctor whose diagnosis includes instructions that a nurse 316 can administer including medicine and time to determine whether the condition changes. If the condition worsens and the rash becomes larger, the instructions may suggest the patient 102 contact physician 326 who is a dermatologist but not until the rash worsens. Alternatively, the instructions may indicate that the patient contact physician 328 or 330 who are emergency and infectious disease doctors, respectively, who may be needed to identify a spider bite or rabies depending on whether the patient experiences a fever or irregular breathing after the initial diagnosis.

Figure 3B:
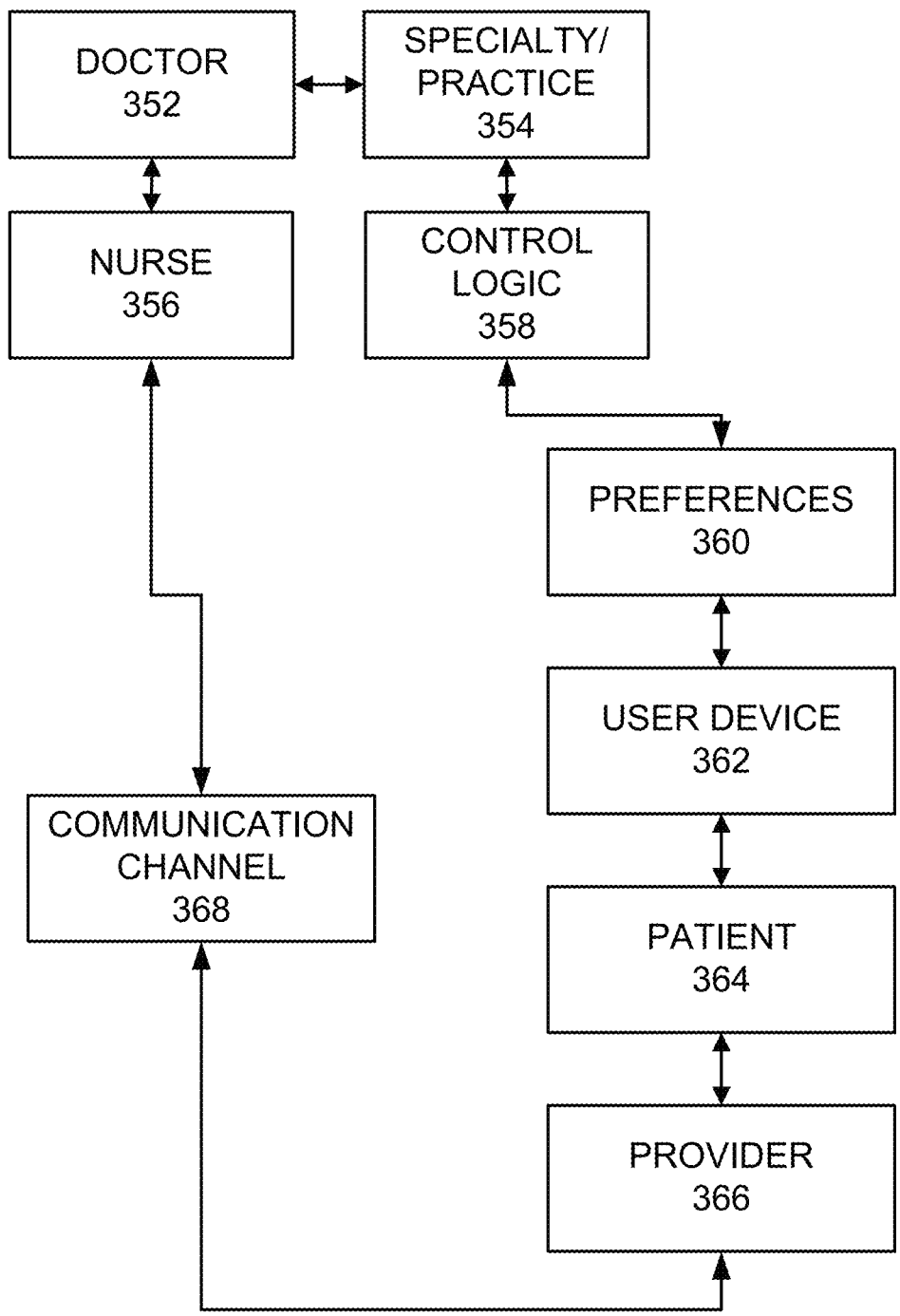
FIG. 3B illustrates an example logic diagram of a patient and physician assignment configuration, according to an example embodiment of the present application.

FIG. 3B illustrates an example logic diagram of a patient and physician assignment configuration, according to an example embodiment of the present application. Referring to FIG. 3B, the logic diagram 350 includes a doctor 352 as an entity that is linked to a particular label, such as a specialty/practice 354. The doctor 352 may also be in communication with a nurse 356 via a computing device on the nurse's communication endpoint and another communication device on the doctor's endpoint 352. The control logic 358 may be used to receive and identify the user preferences 360 for treatment, the user device input 362 of the nurse station or patient symptom capturing device, the patient input 364 (e.g., "I feel pain", "tingling", "my stomach is bloated", etc.), and provider information 366 which identifies the insurance and coverage that the patient is permitted to receive. The communication channel 368 represents the communication between the decision logic and the nurse 356 as an interface that pertains to the patient care.

Figure 3C:
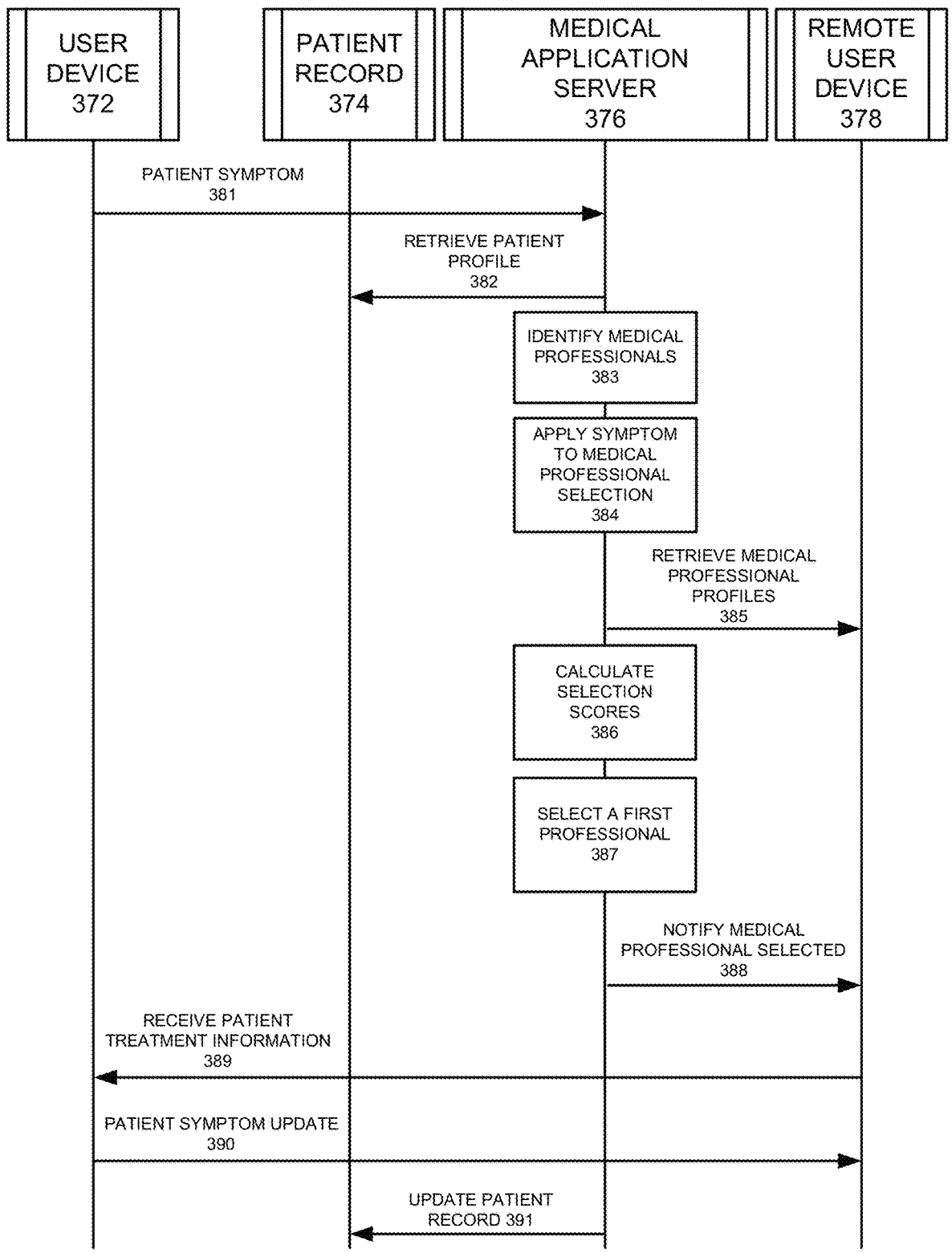
FIG. 3C illustrates an example system communication diagram of a patient and physician assignment configuration, according to an example embodiment of the present application.

FIG. 3C illustrates an example system communication diagram of a patient and physician assignment configuration, according to an example embodiment of the present application. Referring to FIG. 3C, the system diagram 370 may include a user device 372, such as the nurse's computing device which receives the patient symptom via a camera image, video and/or audio capture 381 and provides the data to a medical application server 376. The logic at the server 376 processes the symptoms and provides automatic feedback, physician contact services, diagnosis information, etc. The patient's profile may be retrieved 382 from the patient record source 374 and applied to the present logic to identify medical professionals 383 who are eligible to help the user based on the symptoms, insurance, time of day, schedules, etc.

The symptom information may be used to provide a match to the medical professionals to identify a best selection operation 384. The remote user 378 may be a medical off-site service that communicates with the physicians via a request for service. The remote user 378 may also be the physicians themselves communicating through a computer device. The profiles of the users can be requested and retrieved 385 and used to calculate a selection score 386 that provides the basis for the best candidate physician. Once the score is calculated, the first professional 387 may be selected and applied to the patient request to provide a physician service. The selected physician is notified 388 and is provided with the patient's current symptom list and other related information so a remote diagnosis may be performed. The user device 372 may receive a patient treatment plan from the physician 389 and the user device 372 may offer additional information 390, such as updated vitals, answers to specific questions, additional photos, video and/or audio, etc. The physician can transmit additional instructions and the patient record may be updated 391 to reflect the physician's notes, diagnosis and patient care efforts.

According to an example method of operation, the remote patient and physician selection procedure may include receiving at least one patient symptom at a patient monitoring server and calculating a medical professional selection score based on the at least one patient symptom. The score can be based on relevancy of the physician's skills as compared to the current symptoms experienced by the user. The symptoms may be identified as pertaining to a particular skill set of a physician and matched according to category, portions of the anatomy, pain types, chronic conditions, emergency status of the condition, etc.

The process may also include identifying a plurality of medical professionals having corresponding medical professional profiles based on the medical professional selection score. The scores that are calculated may be limited to the top three, four, etc., or those which are above a certain threshold relevancy level, thus removing the physicians from consideration which are least likely to be the candidate of interest. Also, the method may include selecting a medical professional profile with the highest score, and transmitting a notification to the medical professional selected to identify them as the selected candidate and to encourage the diagnosis begin without delay. The patient symptom(s) received may include at least one of patient history information, a textual description, a photograph, a video and audio data. The method may also include receiving a response message from the medical professional identifying a course of action, updating the patient record to indicate the course of action, and generating a schedule that includes at least one patient interaction based on content of the course of action. The patent interaction may also include at least one of surgery, a medication being administered, blood samples being drawn, blood analysis being performed, and emergency interaction with a physician being scheduled. Additionally, a certainty score may be calculated which is associated with the course of action, and at least one updated patient status may be received. The patient record can be updated automatically and the course of action may be re-evaluated based on the updated patient status and the certainty score may be recalculated based on the updated patient status. The updated patient status includes at least one of a change in vital signs and a change in patient symptoms. Also, the medical professional may be notified of the updated patient status, and as a result, at least one additional response message from the medical professional identifying an updated course of action may be received to address the changes since the last update.

According to one example, when the patient is identified and the symptoms being experienced are logged into the application. Certain logic and/or rules may be applied to select one or more medical professionals as a "target" for routing an initial consult request. The rules may include a broader set of criteria for medical professional selection other than a physician and his or her known qualifications, previous case work, experience, availability, location, etc. For example other rules may include pairing the patient with hospital facilities including transfers to other medical care centers depending on site availability, and wait time, and other physician rules used for selection may include skills offered, distance from hospital, existing contract with hospital, cost, etc. The list of rules may be set by an application administrator to route consult requests depending on the site preferences.

Another example may include offering the receiver of the consult request an opportunity to select a communications channel. For example for a medical professional, upon receiving an alert that there is an inbound consult request the medical professional may select to interact with the requester via the most convenient communication method available. For instance, voice may be selected if the professional is driving, visual IVR may be used if the professional is currently busy on morning rounds, also messaging (SMS) may be used if the professional does not want to wake the person next to them at 2 a.m., etc. All of these interaction types are conveniently integrated with an electronic medical record (EMR), billing systems, and prescription management systems to ensure a thorough accounting of patient care.

Figure 4A:
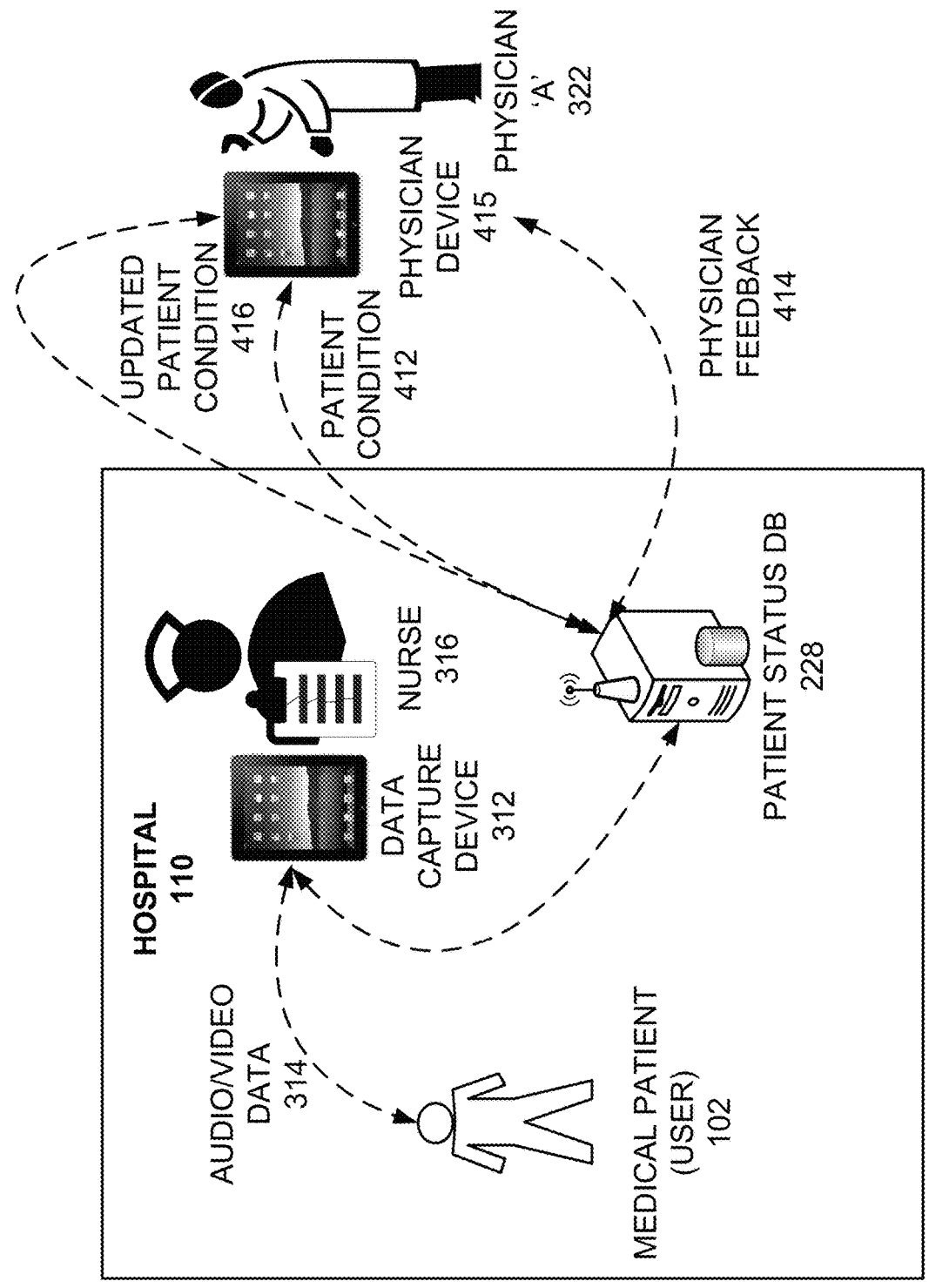
FIG. 4A illustrates an example network diagram of a patient and remote physician treatment configuration, according to an example embodiment of the present application.

FIG. 4A illustrates an example network diagram of a patient and remote physician treatment configuration, according to an example embodiment of the present application. Referring to FIG. 4A, the network diagram 400 includes a similar configuration to FIG. 3A as like reference numerals refer to like elements, however, in this example emphasis is placed on the remote management and patient care of the patient 102 via the selected physician 322. In operation, once the physician 322 is selected from the pool of potential candidates, the patient symptoms and related information can be shared in real-time via audio, video, image, etc. with the remote physician. The decision making as to how to medicate, treat and assist the patient can be performed over a period of time to include an initial patient condition update 412, subsequent patient condition updates 416 and answers to questions posed by the physician 322. Also, feedback can be provided 414 to answer questions and to instruct the nurse 316, the pharmacist, the other assistants, etc. to provide services to the patient.

In one example, the physician may identify a photograph or video of a patient having a swollen face and neck and pale skin. The physician 322 may instruct the nurse 316 to feel the patient's glands around the neck to identify if any are swollen. The information may be communicated via voice or text information and the physician can continue asking questions or immediately set a preliminary diagnosis with instructions for worsening conditions and changes to the diagnosis set to trigger if such symptoms are observed and logged by the nurse. This provides a way to monitor a patient remotely and identify a worsening condition without the physician being present. Of course if the condition does worsen and the patient is diagnosed with a more serious condition via the trigger set in the application operated by the physician device 415.

Figure 4B:
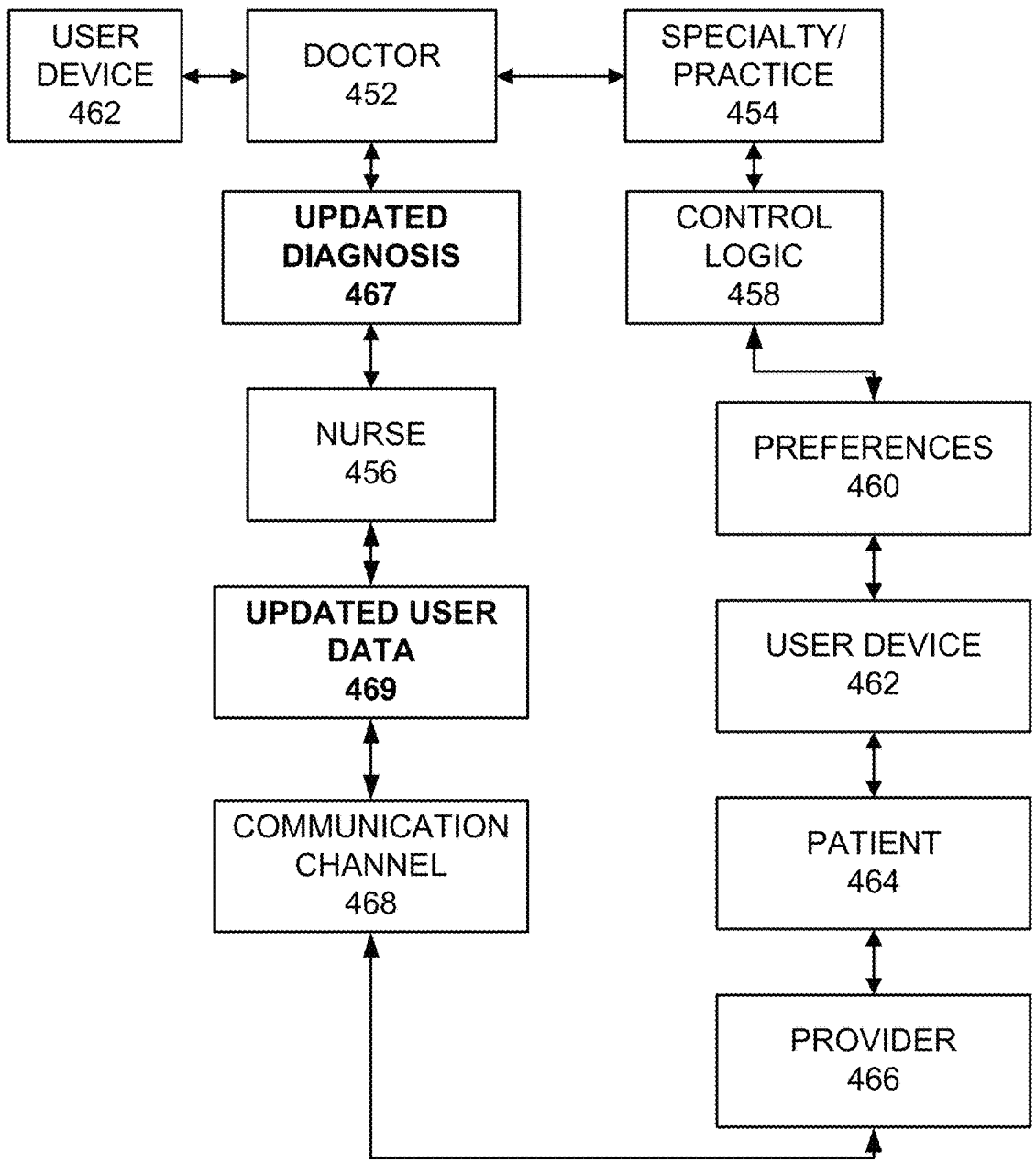
FIG. 4B illustrates an example logic diagram of a patient and remote physician treatment configuration, according to an example embodiment of the present application.

FIG. 4B illustrates an example logic diagram of a patient and remote physician treatment configuration, according to an example embodiment of the present application. Referring to FIG. 4B, the logic diagram 450 includes a doctor 452 linked to a particular specialty or practice area 454, the control logic 458 may identify an appropriate physician based on information associated with the input information (e.g., video, keywords, tags, etc.). The user and physician preferences 460 may be retrieved from memory and applied to the session to provide options and services that are accommodating to the preferences and options available. The user device 462 may be any computing device operated by the patient/nurse/medical assistant. The device may be capable of capturing the patient symptoms and formatting them into a patient profile accessible to the physician application and the provider requirements 466 for updating, compliance, billing, etc. The communication channel 466 provides a channel to communicate the data, such as a wireless/wired secure Internet connection.

Throughout the patient update and diagnosis/treatment procedure, the updated user data 469 may be transmitted to the physician periodically based on a fixed schedule or based on a physician required schedule. For example, the physician may be concerned about certain symptoms and may setup a logic trigger, such as if patient fever exceeds 101 degrees in next 24 hours then transmit images of the skin rash every hour thereafter until the fever is reduced below 101. This automated physician requirement can cause updated user data 469 to be requested to a nurse station, a video camera in the patient's bedroom to take still images and upload them automatically, etc. The nurse 456 may be accessible via the user device 462 and may be part of the updated user data 469 entry and the reception of the updated diagnosis 467, which may be transmitted as an alert. The alert information can be parsed for certain actions the nurse is required to perform based on the updated diagnosis (e.g., medications, procedures, vitals to be checked, video or image captures, etc.).

Figure 4C:
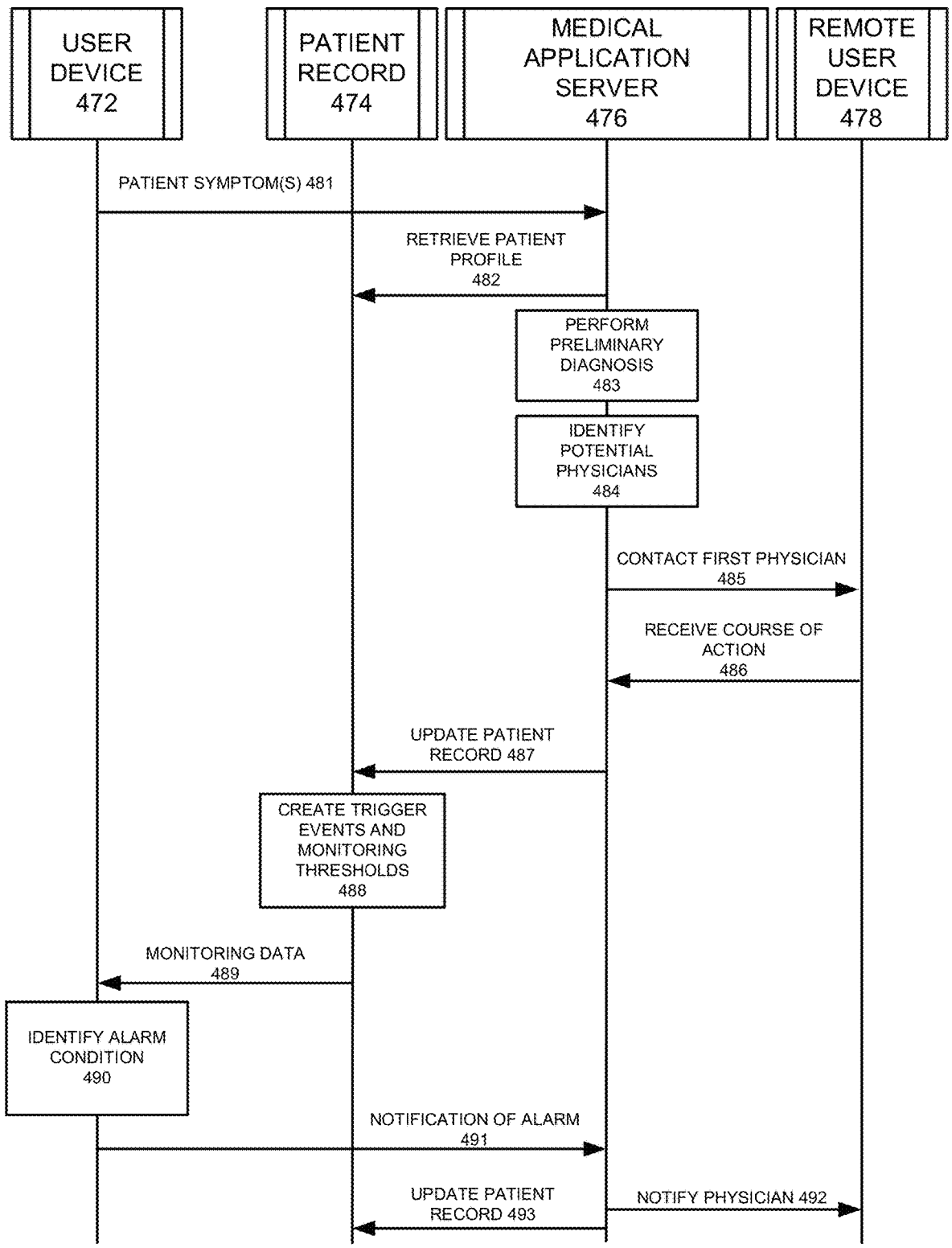
FIG. 4C illustrates an example system communication diagram of a patient and remote physician treatment configuration, according to an example embodiment of the present application.

FIG. 4C illustrates an example system communication diagram of a patient and remote physician treatment configuration, according to an example embodiment of the present application. Referring to FIG. 4C, the system diagram may include two endpoint devices including a user device on the patient side 472 and a remote user device 478 on the remote physician side. The patient record 474 may be a data file stored at a particular location and retrieved in response to certain action taken by the user devices. The medical application server 476 may be used to store the application, such as a cloud server application and a memory databank to record updates, changes and other secure information necessary to perform ongoing patient services.

In operation, one or more patient symptoms are identified, captured via a data capturing device and received 481 at the patient monitoring server or medical application server 476. The application server may then log or generate a preliminary diagnosis 483 of the patient's condition with at least one known medical condition based on the patient symptom(s) received. The patient record may be retrieved 482 to associate the updated patient data with the current diagnosis and conditions. The potential physicians are identified 484 as candidates based on their credentials and specializations. A selection may be performed and the physician selected may be contacted 485 to share the patient information available. The physician may then provide a course of action 486 that includes instructions, thresholds which cause additional instructions or triggers and/or requests for additional information.

The course of action and other instructions 486 may be received and used to update the patient record 487, which may then initiate the trigger(s) and events 488, which form the basis for the patient monitoring efforts to perform in the present and the future.

The monitoring data 489 may include procedures, medications, instructions, concerns, etc. that need to be addressed by the personnel caring for the patient. The user device 472 used to monitor the patient may then be setup to identify a particular condition alarm 490, such as a change in patient vitals, a worsening wound or existing condition, patient temperature, etc. A notification alarm will be triggered 491 to notify the application server 476 which may in turn notify the physician 492. The patient record 493 should be updated at each stage of the procedure to ensure the records are accurate and available for all interested parties.

The patient symptom(s) received may include at least one of patient history information, a textual description, a photograph, a video and/or audio data. In addition, the patient record may be updated to indicate the course of action to perform. The course of action may initiate a number of vital health thresholds to be generated which correspond to the patient's vital statuses, and apply at least one alarm condition that is set to trigger if at least one of the plurality of vital health thresholds are exceeded. The alarm condition may be set to trigger based on a period of time, if a prescribed medication, treatment, procedure, etc., is not logged as having been administered and/or if a predefined condition occurs. A cautionary status notification may be transmitted to a receiving device of a health care professional presently on-call, the cautionary condition status notification may indicate that the predefined condition has not yet been associated with the patient and if the predefined condition does occur and is logged, then the medical care condition diagnosis may be changed to a new medical care condition.

In another example, a new notification may be transmitted to a new communication device of a new medical professional different from the medical professional contacted previously, such as in the case of an elevated condition requiring referral to a different type of physician. The new medical professional may be identified via a medical professional profile that provides a match to the new medical care condition parsed from the new notification message. As a result, that new physician may receive an immediate update of the patient status, severity of condition, and/or an invitation to respond to the current patient status. At least one additional response message may be received from the new medical professional identifying an updated course of action.

Figure 5A:
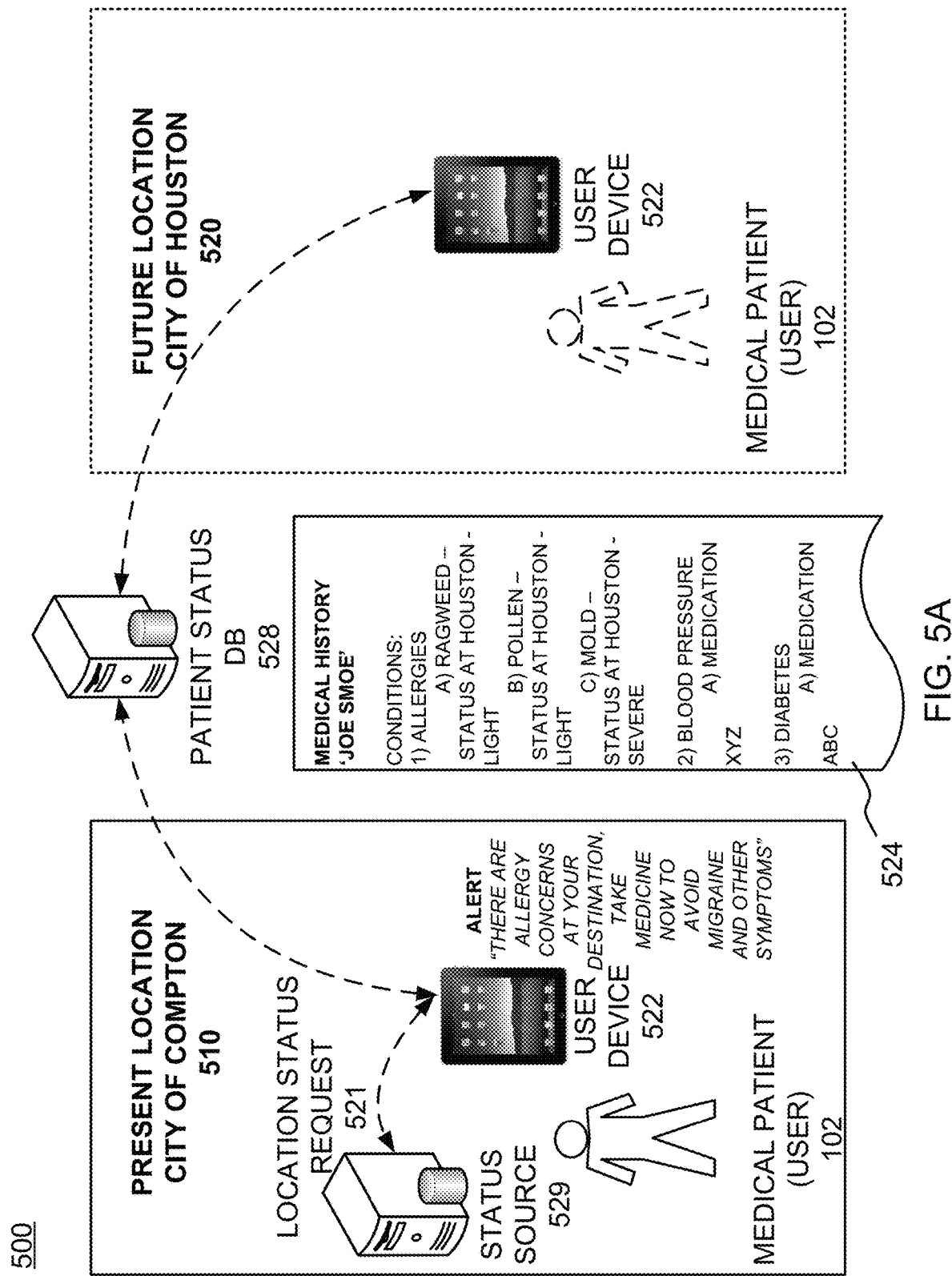
FIG. 5A illustrates an example network diagram of a predictive patient health alert configuration, according to an example embodiment of the present application.

FIG. 5A illustrates an example network diagram of a predictive patient health alert configuration, according to an example embodiment of the present application. Referring to FIG. 5A, the configuration 500 includes a present location of the user 'city of Compton' 510 where the user 102 is registered as living or residing most of the time. The user is identified via his or her user device 522 from a GPS coordinate location technique or power estimation from cellular communication towers (i.e. triangulation).

In operation, the user may be periodically audited via a user health monitoring function that operates to identify any potential threats to the user's well-being. For example, the user device 522 may be in communication with a status source database 529 which maintains the user's medical records and which monitors the user's prescriptions to ensure they are automatically filled ahead of time, and whether certain local factors are present which could affect the user's health. For instance, if a snow storm is headed towards the Compton 510, a medication audit could take place to ensure the user's prescriptions are filled if they are low and the storm will likely create a condition where the pills can't be refilled for several days due to an inability to reach the pharmacy. Another example may include reminders, such as a condition that allergies are likely to be much higher on a particular day or the next day from a weather report, the application could create an alert to have the user take an allergy medication the day before to avoid waking up with a migraine or sneezing.

A status request may be initiated from the user's mobile device 522 to an application server which seeks location specific information (i.e., weather, allergies, holidays, etc.) and compares the information to the user's present health conditions to determine whether an action must be created to protect the user. The patient status database 528 may provide details regarding the patient's current health problems, conditions or concerns. The patient's health information and the current status information may cause an alert to be created and transmitted to the user to inform the user to take a medication, approve a mediation refill, confirm a pharmacy location that is convenient, etc. The user's medical history 524 includes various user conditions which can easily be paired or matched with current environmental conditions identified from a notification service. In one example, the user may be booked to fly to Houston 520 the next day, in which case a periodic audit from the patient status DB 528 would yield a calendar status check operation or other comparable operation that would identify the destination and would in turn perform a notification check of the conditions in the destination city, which are received and compared to the user status DB 528 to identify potential concerns, such as allergies, pharmacy locations, availability of a particular drug, current quantities a user may have of a particular drug, etc.

Figure 5B:
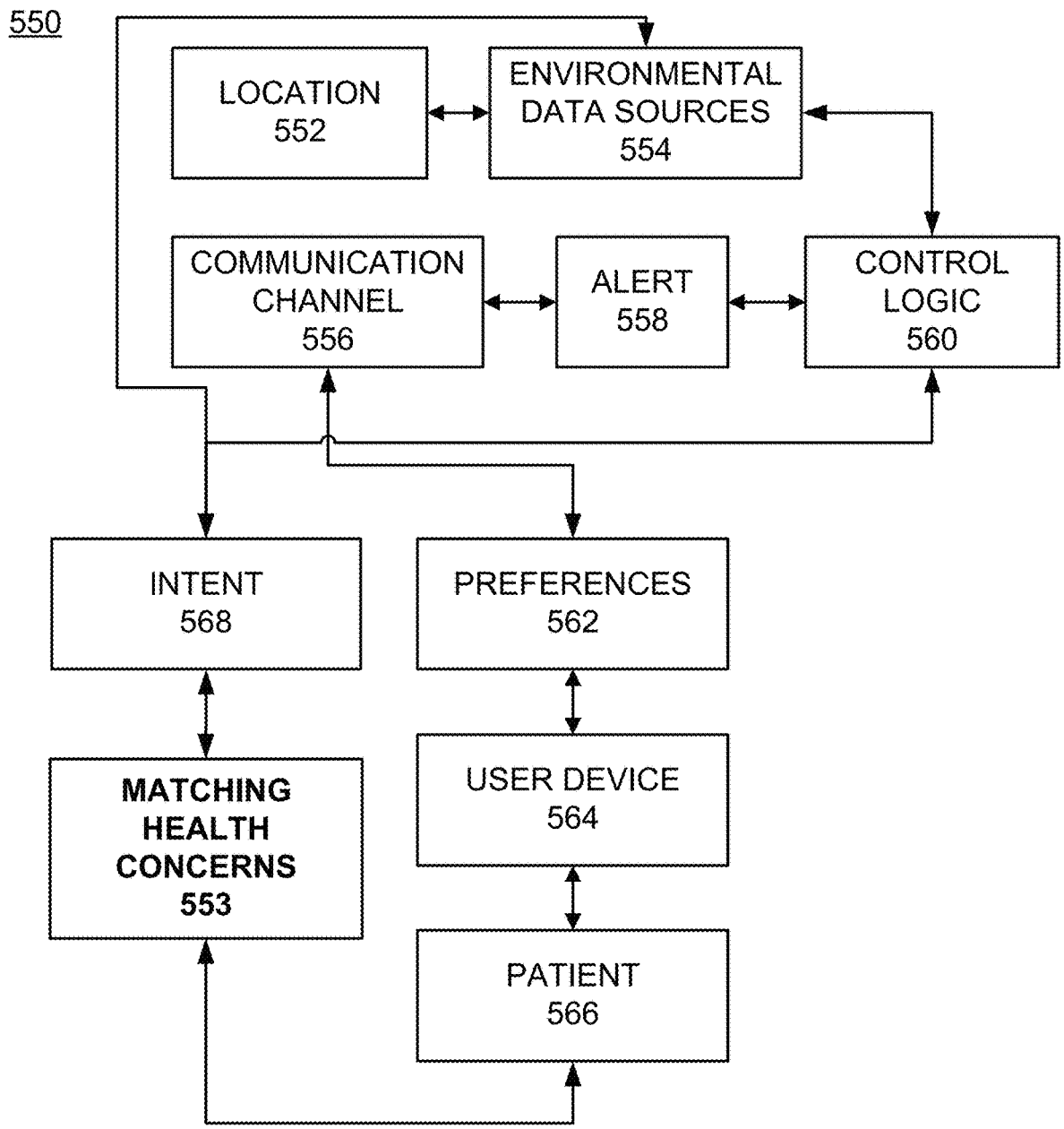
FIG. 5B illustrates an example logic diagram of a predictive patient health alert configuration, according to an example embodiment of the present application.

FIG. 5B illustrates an example logic diagram of a predictive patient health alert configuration, according to an example embodiment of the present application. Referring to FIG. 5B, the logic diagram 550 includes various logic entities which may be part of the alert condition and user status identification application. A location 552 may be linked to the user and present environmental data sources 554. The control logic 560 may represent the processes or operations that are set to be performed including receiving location information notifications, retrieving the patient health information and determining whether an alert 558 should be generated that could be beneficial to the user's health. A communication channel 556 represents the wireless medium and/or Internet connection used to connect with the user to exchange information and provide messages to the user device. The preferences 562 may be user preferences that can be referenced prior to generating an alert to include the user's preferred actions (i.e. automatic prescription refill, store preference, generic drug vs. name brand etc.), contact preferences (e.g., email, text message, telephone, etc.). The user device 564 represents the mobile computing device operated by the user and the patient 566 is the user who is being identified and is the subject of the actions and alerts. The intent 568 may be the goals or underlying strategies that are sought by the application (i.e., patient health, patient money saving, patient time saving, etc.) and may be based on the user preferences.

Figure 5C:
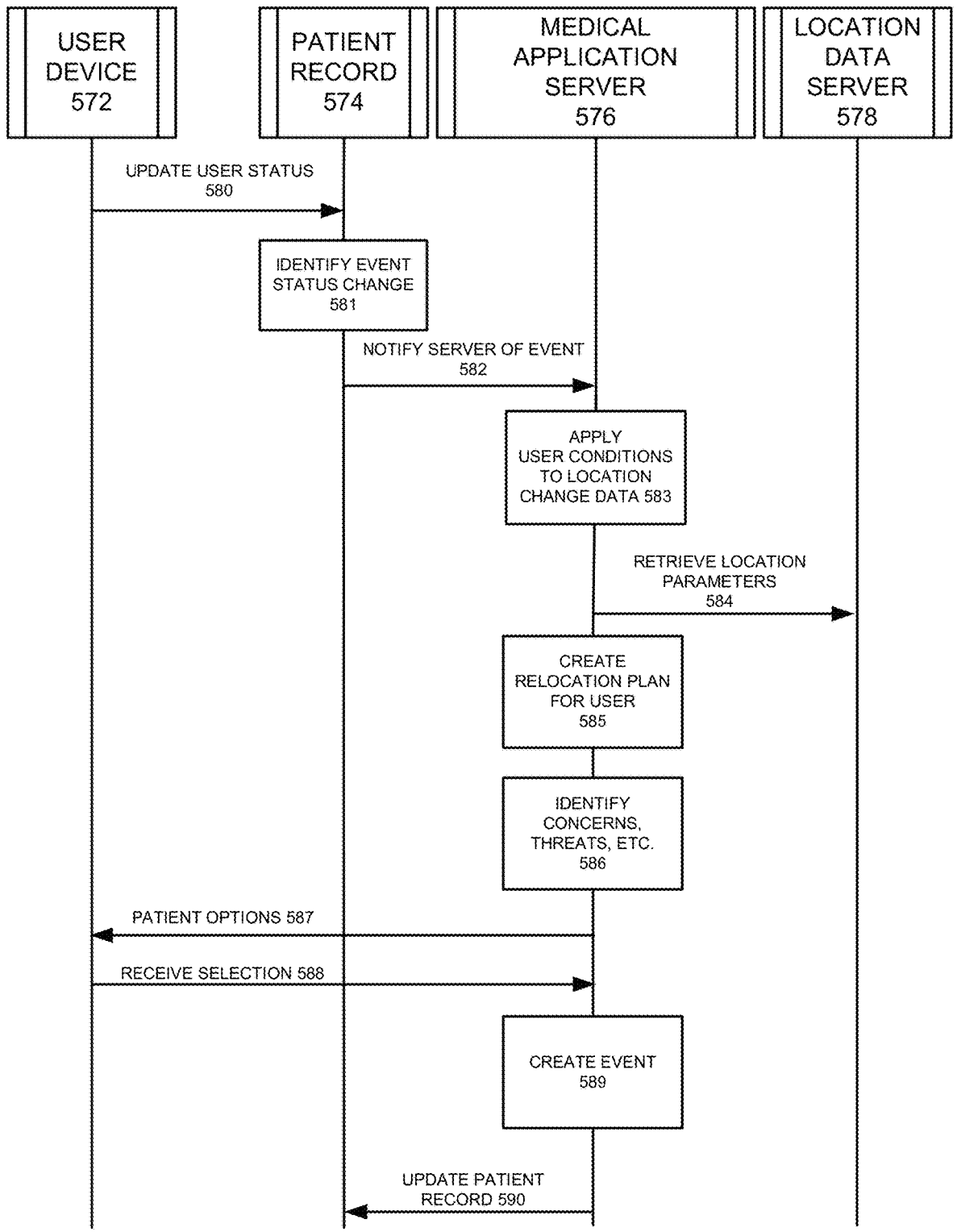
FIG. 5C illustrates an example system communication diagram of a predictive patient health alert configuration, according to an example embodiment of the present application.

FIG. 5C illustrates an example system communication diagram of a predictive patient health alert configuration, according to an example embodiment of the present application. Referring to FIG. 5C, the system configuration 570 may include a user device 572 which is the contact device for the user. The patient record 572 may store user conditions and preferences. The medical application server 576 may be a remote cloud based application server that maintains the user's profile and provides the decision logic to assist the user and would likely be an application hosted by the user's insurance company or hospital group. The location data server 578 represents a third party data source that provides alerts and other information to the medical application server to identify any user concerns or threats.

In one example method of operation, the user information parameters may be stored in a user profile of a user or a patient record 574, the information can be updated to be current 580 and may include additional information or changes. The patient record 574 may identify an event status change 581, such as a future location status associated with the user profile of the user (i.e., travel plans). The patient record change may be updated to notify a server 576 of the event status 582. Certain user conditions can be applied to the anticipated location change 583. A request 584 may be sent to at least one data source 578 to provide updated location status information associated with the future location. A relocation plan 585 can be created for the user when he or she arrives in the new location. The location, the user conditions, and any geographical concerns may all be part of the procedure used to generate an alert. The alert may be created and the user may receive certain options 587 which can be selected via a user interface on the user device 572.

Assuming a selection is made, the user selection may be sent back 588 to the server for the action to be performed. The event may then be created 589 to fill a prescription, create a reminder, etc. The patient record may than be updated 590 to reflect the changes. Additionally, updated location status information may be received at any time to modify the current status of the application. The updated location status information may be used to compare to the user information parameters to identify a match and a corresponding action to perform. The user information parameters may include at least one of known user health conditions, user preferences and user health insurance information. Additional operation may include retrieving a travel reservation associated with the user profile to identify an anticipated change in location. Also, the location status information associated with the future location may identify a condition that is a threat to the user's health based on the match of the updated location status information and the user information parameters. An alert may be generated based on the threat to the user's health, and transmitted to the user device operated by the user. The content of the alert may be parsed and the application may be initiated to provide remedy information related to the threat, an additional alert may be generated that includes the remedy information and the additional alert may be transmitted to the user device. The remedy information includes medication information that could alleviate the threat and at least one location where the medication can be purchased and/or locations of at least one of a pharmacy, a hospital, a medical clinic, and link information for access to hours and contact information of medical facilities.

Figure 6A:
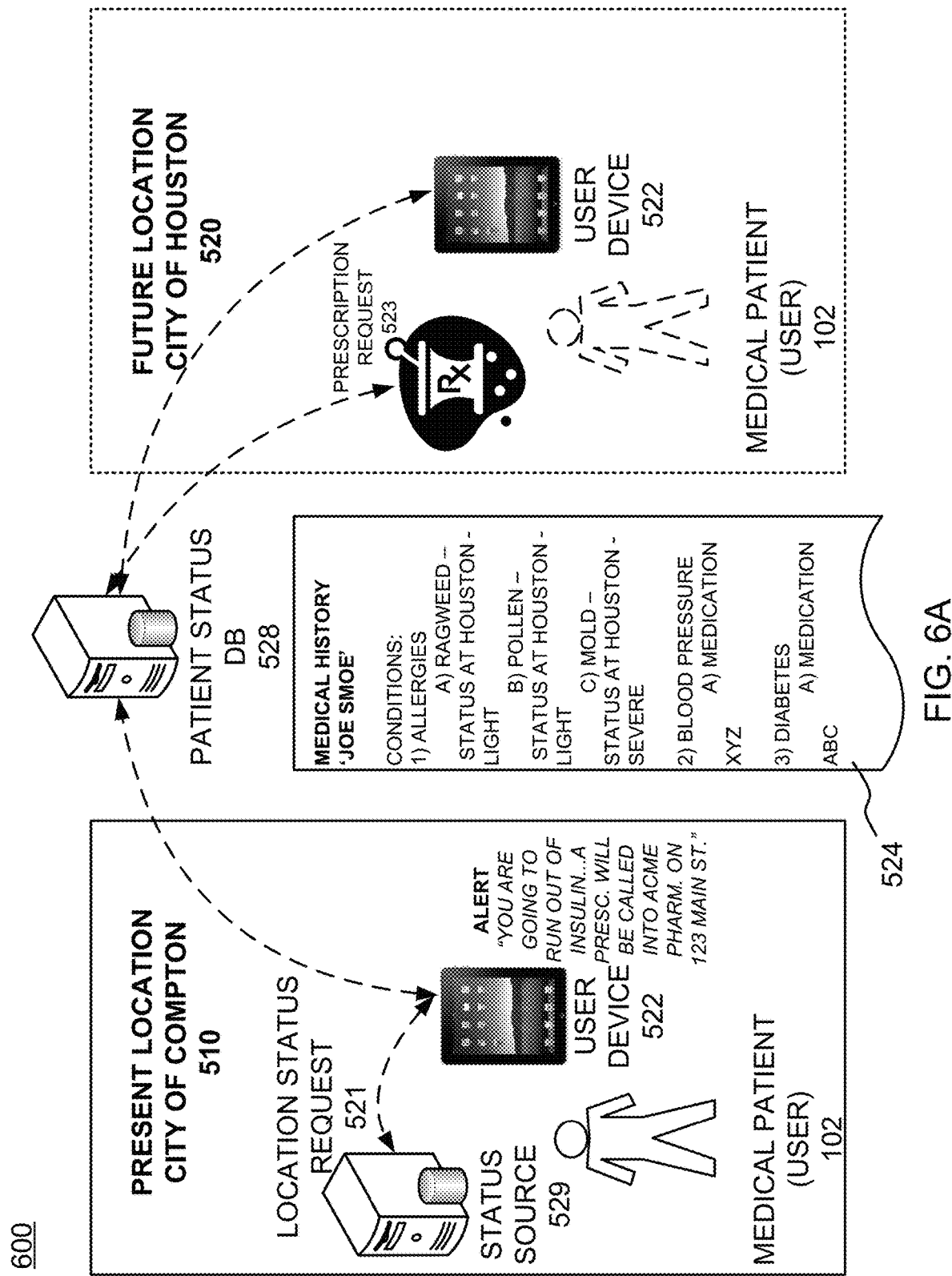
FIG. 6A illustrates an example network diagram of a predictive patient relocation health alert configuration, according to an example embodiment of the present application.

FIG. 6A illustrates an example network diagram of a predictive patient relocation health alert configuration, according to an example embodiment of the present application. Referring to FIG. 6A, the configuration 600 includes like numerals and references to FIG. 5A. However, in this example, the patient status DB 528 identified a threat or concern, such as allergies in the new location or that user is about to run out of a current prescription and will need to obtain a refill at the new location. For example, the application may identify the prescription needed, identify pharmacies 523 near the location of the user's destination in Houston 520 and enable a prescription refill automatically according to the user preferences to perform such automated actions.

Figure 6B:
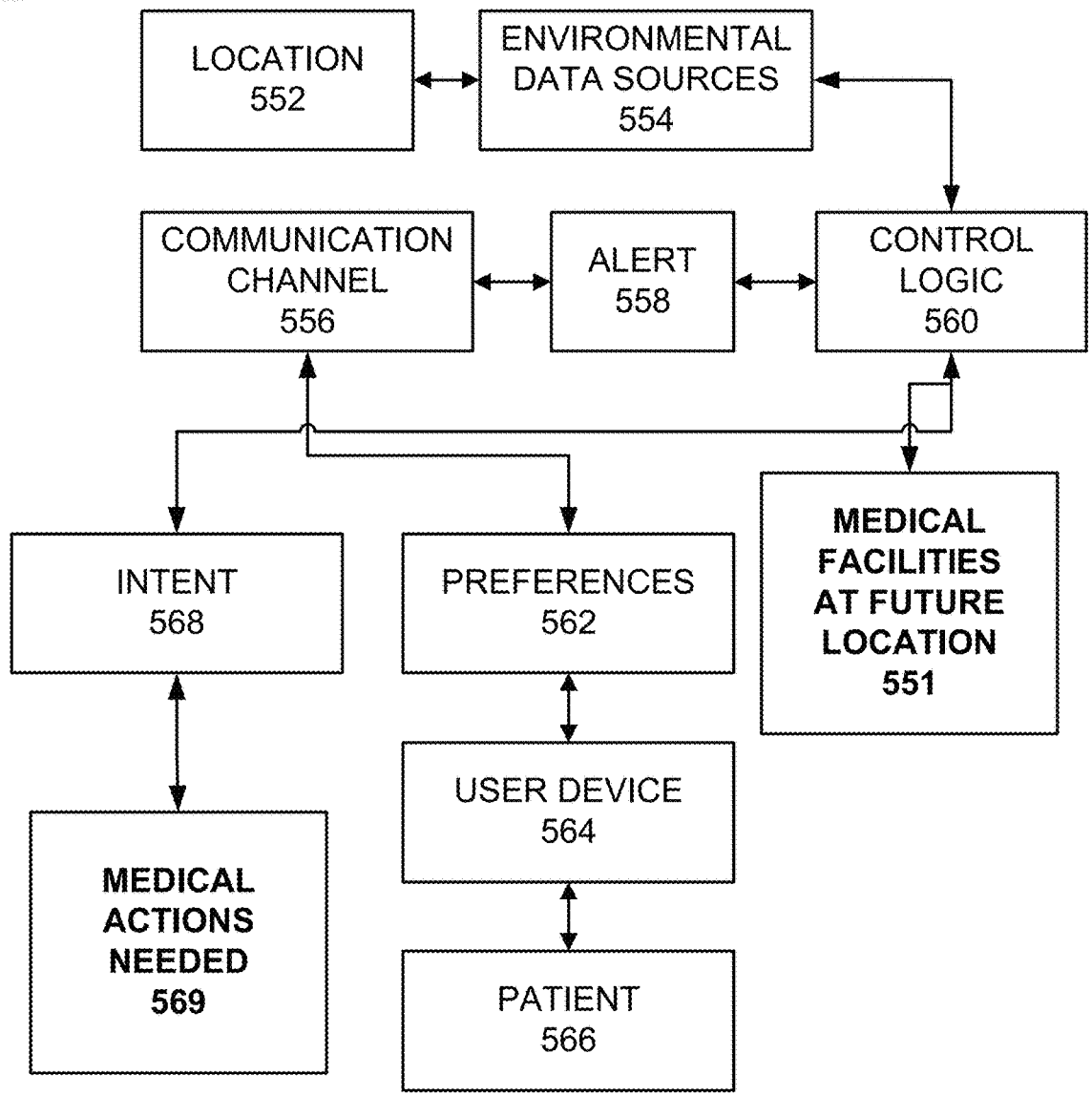
FIG. 6B illustrates an example logic diagram of a predictive patient relocation health alert configuration, according to an example embodiment of the present application.

FIG. 6B illustrates an example logic diagram of a predictive patient relocation health alert configuration, according to an example embodiment of the present application. Referring to FIG. 6B, like references and numerals refer to like elements in FIG. 5B. The logic diagram 650 includes additional logic elements medical facilities at future location 551 and medical actions needed 569. Those elements enable the control logic 560 to identify locations that can accommodate the user's prescriptions, medical care facilities, insurance, etc. For example, if the user is fragile or has been experiencing severe health conditions, the medical care facilities at the destination which offer care and medicine for the user's current condition and which are compatible with the user's insurance information may be identified and extracted prior to the user traveling. Prescriptions, appointments, screenings and other processes may be performed at the new location prior to the user arriving.

Figure 6C:
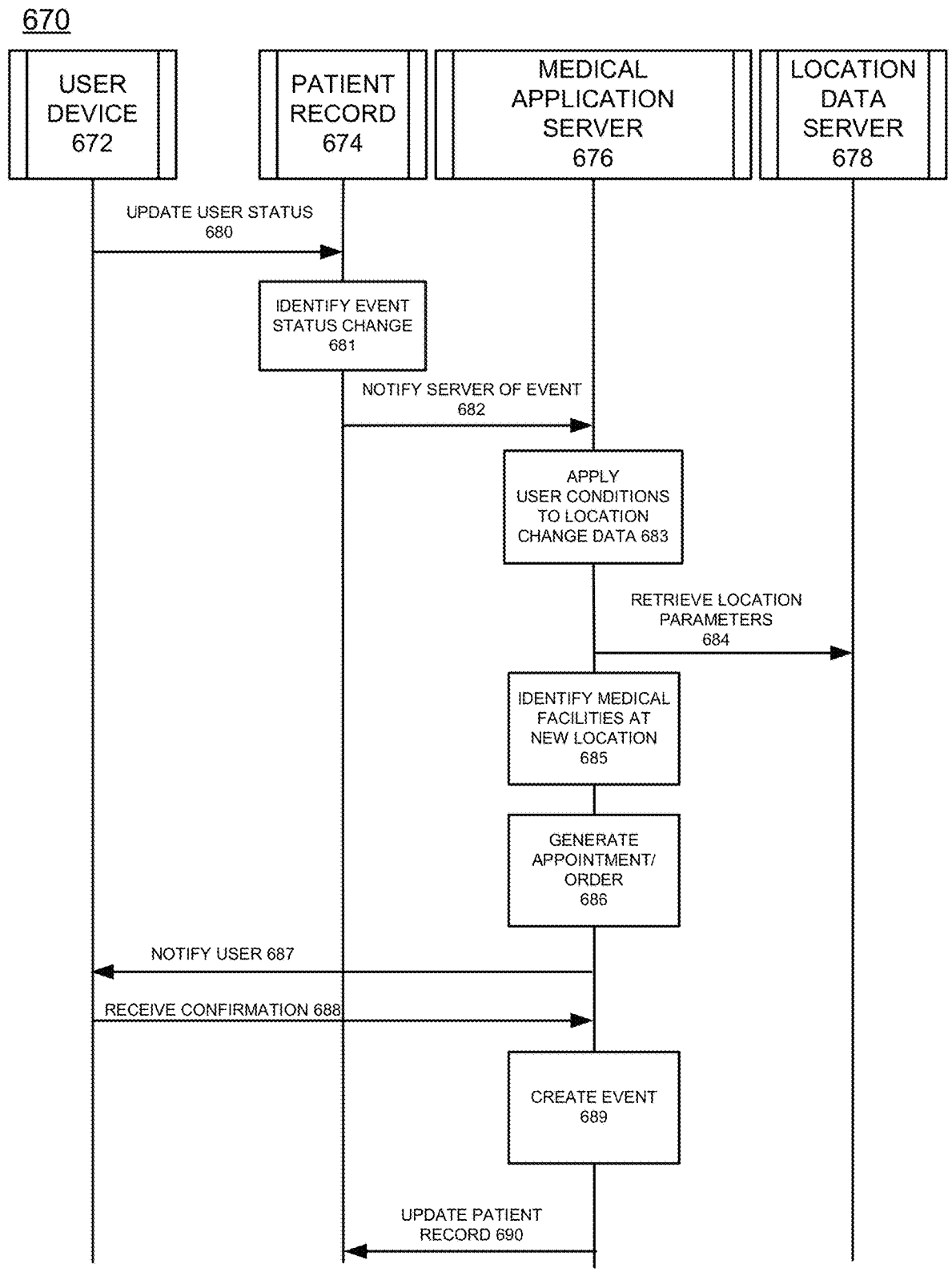
FIG. 6C illustrates an example system communication diagram of a predictive patient relocation health alert configuration, according to an example embodiment of the present application.

FIG. 6C illustrates an example system communication diagram of a predictive patient relocation health alert configuration, according to an example embodiment of the present application. Referring to FIG. 6C, the user status may be updated 680 at any time for any reason, such as changes or new statuses to report on a periodic basis (e.g., once an hour, once a day). The patient record 674 may reflect the changes and/or identify a new event 681 that requires consideration. The server 676 may be notified of the event 682 so user conditions and preferences can be applied along with third party location and status information 683. The location server 678 may provide various updated data parameters 684 which could trigger an event or action to initiate via the user application. For example, the need to identify medical facilities at a new location 685 may be enacted and an appointment/order may be initiated automatically 686 based on the user's needs. The user device 672 may be notified 687 and the user may perform a selection which is sent as a confirmation 688 to the application server 676. As a result, an event is created 689 and the patient record 674 is updated 690 to reflect the changes.

According to an example method of operation, the user information parameters may be stored in a user profile of a user and updated each time a change occurs or according to a fixed schedule. Changes in status can be anticipated and identified via an audit procedure or application crawler that audits reminders, events, and other organized and stored information pertaining to the user. The example may also include identifying a future location status associated with the user profile of the user, identifying medical facilities within a predefined area of the at least one future location status, and initiating a medical action associated with at least one of the medical facilities and the user information parameters in the user profile. The user information parameters include at least one of known user health conditions, current prescriptions, user preferences and user health insurance information. The medical action may include transmitting a prescription refill request to the medical facility prior to the user traveling to the new location. Other operations may provide retrieving a travel reservation associated with the user profile and identifying the future location status in the at least one travel location as being in a different location than the current location of the user, retrieving the location status information associated with the future location, and identifying the a medical action as having a time period that includes the user being located at the travel location. Examples of the medical action may be requiring a doctor visit, treatment, prescriptions, etc. The application may generate an alert including the least one medical action, and transmitting the alert to the user device operated by the user to inform the user of the scheduled event. The method may also include parsing content of the alert and initiating an application that provides location information of the medical facility and generating an additional alert that includes the user's appointment and prescription information created by the medical action, and transmitting the additional alert to the user device. The medical condition may include a chronic health condition with at least one medication requirement.

Figure 7A:
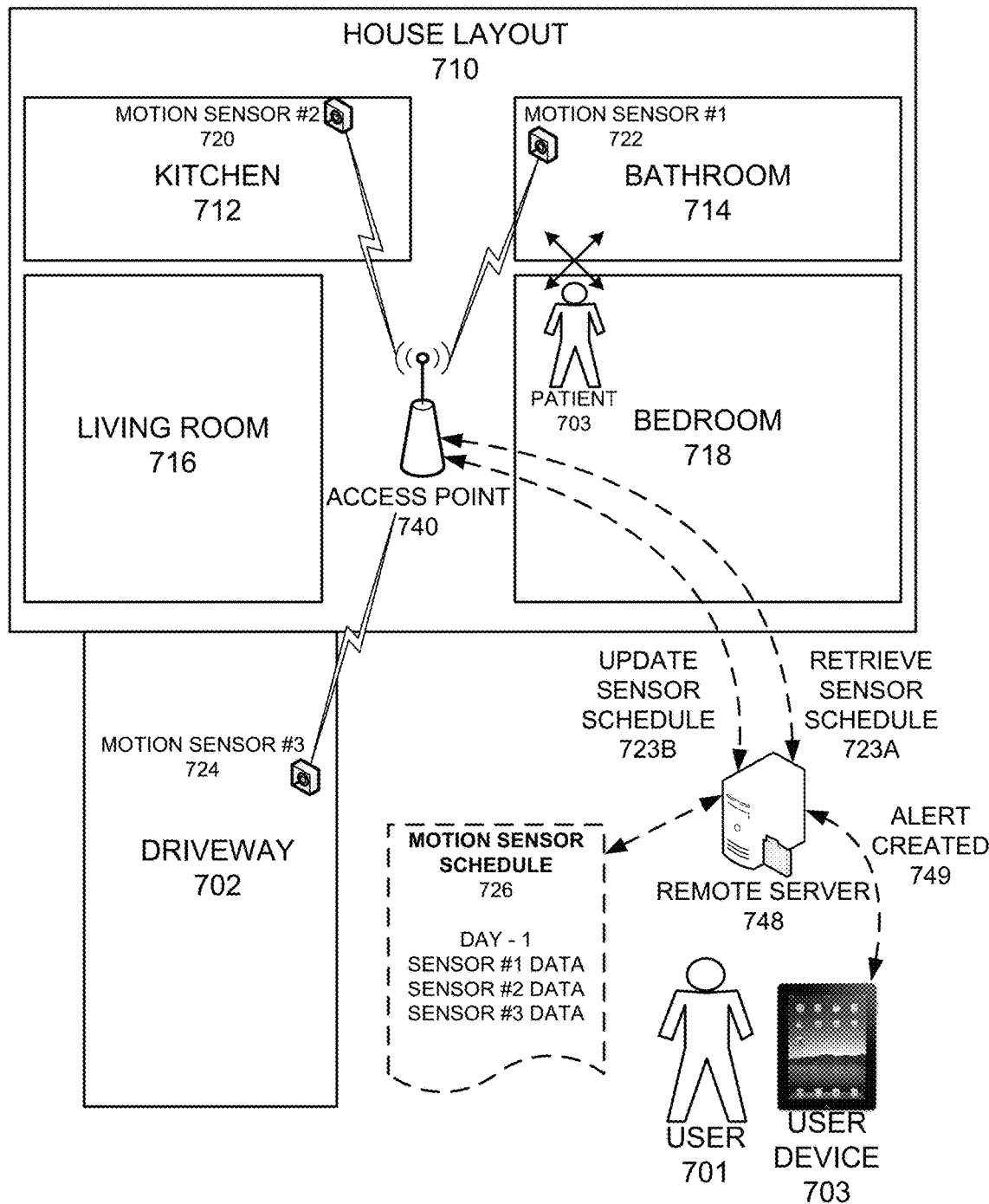
FIG. 7A illustrates an example network diagram of a patient monitoring configuration, according to an example embodiment of the present application.

FIG. 7A illustrates an example network diagram of a patient monitoring configuration, according to an example embodiment of the present application. Referring to FIG. 7A, the network configuration 700 includes a house or living quarters with various sensors used to identify motion triggered by a patient or user being monitored. The house layout 710 includes various rooms or location some of which have sensors to track user movement, patterns and to ensure the patient is maintaining their well-being.

The kitchen 712 has a motion sensor 720 to ensure the patient 703 is identified if he or she moves into the kitchen to perform any such task, such as cooking, cleaning, lounging, etc. Also, the bathroom 714 also has a motion sensor 722 to identify the patient 703 accessing the bathroom as one way to identify a healthy daily routine as opposed to not visiting the bathroom. Additional sensors may be placed in the hallway, bedroom 718, living room 716, outside near the driveway 702 of the house (sensor 725), etc. to communicate with an access point 740 via a wired or wireless communication medium and provide frequent updates of non-events or actual triggered motion events. The access point may communicate with a computer that forwards the sensor data to an off-site server 748 that is configured to receive updated sensor data 723B and retrieve 723A and update a corresponding schedule 722 and process the data to determine whether an alert must be transmitted to an interested party 701 via the user device 703.

In the configuration 700, patient 703 is the subject of the monitoring operations. The patient 703 may be a known subject, such as an elderly person who is being tracked for their own personal safety and health or an unknown person who may have entered a home or premises that are being monitored to avoid unauthorized persons from accessing the premises as a security measure.

In one example, the patient 703 may walk past a motion sensor 720 that is wired to a device detection unit or which has a BLUETOOTH interface that transmits a signal to a receiving unit or access point 740 that an event has been triggered (i.e., the motion sensor has been tripped or activated). The receiving unit or access point may be a router, a wireless access point, a remote communication base station, etc. (not shown). The communication protocol may be BLUETOOTH® or a 3G/4G cellular communication standard that transmits a wireless signal to indicate that the sensor has been activated. A local communication TX/RX device may receive the sensor activation(s) instances and time stamp those events, store those events, and/or transmit those events to the access point for immediate communication relay to a remote server. In operation, the server that receives the sensor activation information over the Internet, stores the information in a user profile account and then applies business rules to determine when a subscriber should be notified of the sensor event depending on the preferences available in their personal profile (e.g., notifications for each sensor activation, notifications for no sensor activation in a 12/24 hour period, etc., specific times associated with the sensor activation, etc.).

A few examples of a patient 703 activating a motion sensor may include a subscriber initiating an audit application for receiving a notification that the event has occurred, and/or receiving a notification that an event has not occurred within a predefined time interval (e.g., 12 hours since anyone at grandma's house has entered the bathroom). Another example provides that a specific number of hours 'X' has passed since the last event or sensor has received information or has been triggered, where the value of 'X' is set by the subscriber.

In this example, an adult may be monitoring their elderly parent and may desire to know if 8 hours passes before the bathroom sensor is triggered indicating a potential problem with the elderly parent if 8 hours has passed with no sensor indication in the bathroom. Other examples may provide a notification being sent if someone has triggered another sensor by the front door of the house and/or a notification may be sent if a person or car has entered the driveway 702 via a driveway sensor 724 and/or a traffic pattern sensor at a remote location or at the house identifying if the amount of traffic has increased.

The network 700 illustrates the layout of a single-story home with three sensors (720, 722 and 724) currently activated. The house layout 710 has four rooms 712-718 and two of which have sensors installed. For example, the subscriber may have setup one sensor 720 in the kitchen 712 and another sensor 722 in the bathroom 714. The sensors may be battery power transmitters with sensors that detect light, movement, sound or other state changes, such as temperature, precipitation/moisture, heat, etc. The sensors may also be plugged into the wall outlet receptacles to provide constant power needed to transmit a signal to the local receiving device and/or access point 740. The driveway 702 may have a sensor 724 installed near the driveway to indicate if a person has walked up the driveway or a car has entered the driveway.

In operation, any time one of the sensors has identified a sensor trigger, which for this example will be movement, the sensor may transmit a wireless communication signal to a small receiving box or device that is in communication with the communication access point 740. The indication may provide a unique sensor identifier so it is clear which sensor has transmitted that indication and a timestamp may be linked to that particular sensor indication (e.g., sensor #2 has triggered a sensor indication at 8:15 am on Monday Feb. 23, 2014). The sensor indication may also be used to map the sensor to a predefined territory, such as a name entered into the application system (i.e., kitchen, bathroom, driveway) during the online setup that links the sensor indication or being triggers to the sensor ID number of that sensor. The access point 740 may, in turn, periodically transmit the updated data to a remote server 748 that links the sensor IDs to a particular user account so the notifications may be created accordingly (e.g., automated phone calls, text messages, emails, notify EMS-911, etc.). The sensor update operation may be sent to the server 748 that stores the subscriber data profile which can be accessed and updated to include the recent indication or trigger, and which is also linked to an automated notification engine that transmits a call/email/text message to the predefined subscribed entity 703 depending on the preferences in the subscriber profile. In this example, the user 701 is likely to be an assigned chaperone or kin of the patient who is concerned about the daily well-being of the patient and who is likely to call the neighbor or 911 if something appears to abnormal or wrong with the patient's current activity.

Figure 7B:
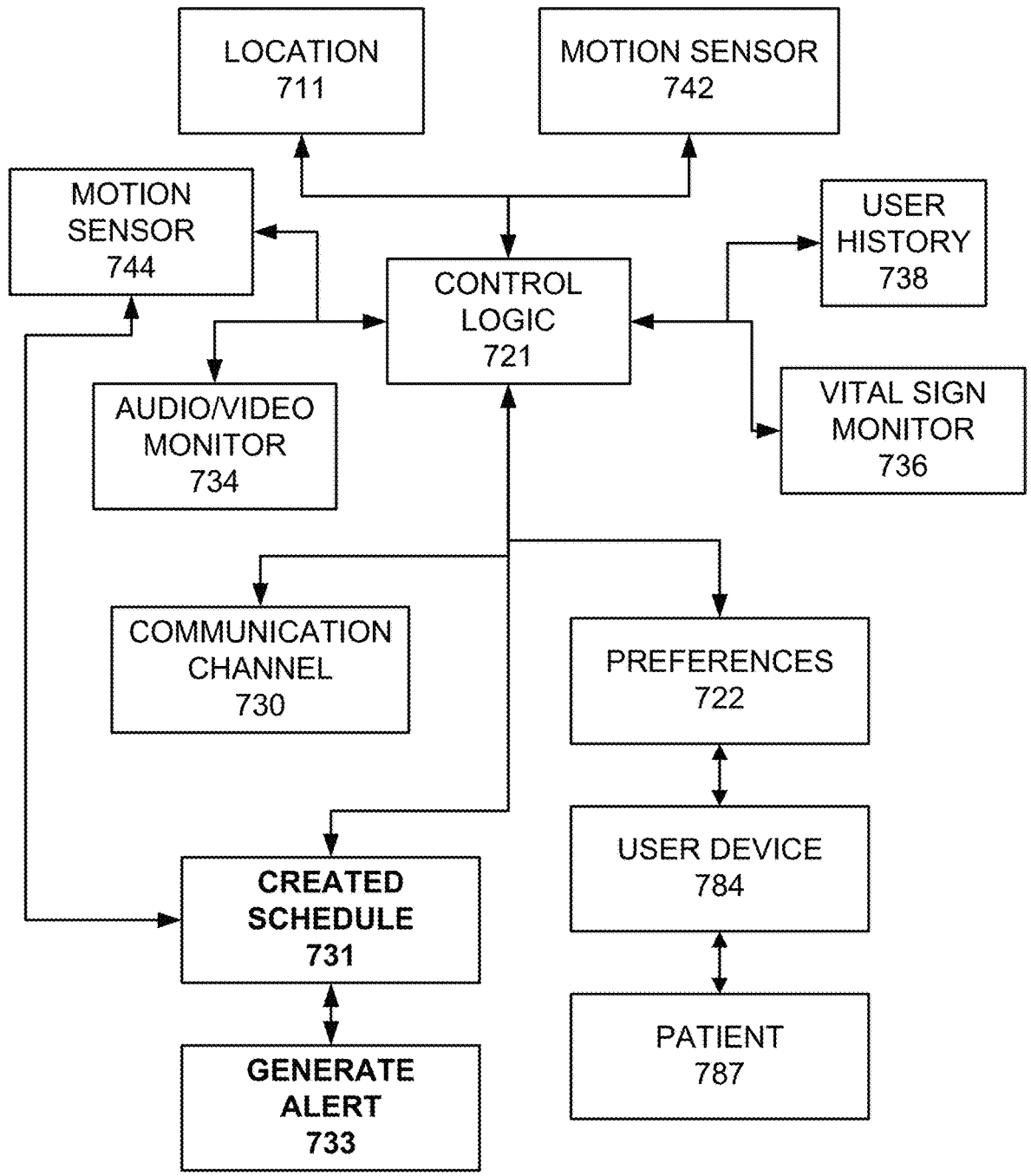
FIG. 7B illustrates an example logic diagram of a patient monitoring configuration, according to an example embodiment of the present application.

FIG. 7B illustrates an example logic diagram of a patient monitoring configuration, according to an example embodiment of the present application. Referring to FIG. 7B, the logic diagram 725 includes various parameters of information and corresponding logic decisions which may be part of a result that saves lives and alerts user devices subscribed to identify problems with a patient being monitored. For example, the control logic 721 may identify a location 711 of the sensor data and the various motion sensors 742 based on identifiers associated with the sensors and the computer/application operating at the residence which identifies the location, the user, the profile, the schedule, the customized settings, etc. When sensor data is triggered (e.g., motion triggers, video triggers, image triggers, audio triggers, etc.), the user history and schedule 738 can be retrieved from memory and may be updated to populate a daily schedule or other predetermined event. Vital signs and patient worn monitoring devices 736 and sensors may also be part of this monitoring process to identify patient health. In general, motion sensors 744 and/or an audio/video monitor 734 may provide feedback and information necessary to update a schedule and create alerts if necessary. The communication channel 730 provides a medium to communicate the information from the sensors and access point to the remote server. User preferences 722 may be applied to an alert decision and the user device 784 may be identified by a telephone number, email, etc. that is linked to the patient 787 being monitored. In general, the data may be received and used to create and update a schedule 731 so an alert can be generated 733 in the event the schedule is not properly met or populated on a periodic basis (e.g., grandma did not trigger any sensors in the house this morning 9 am-11 am=generate alert).

Figure 7C:
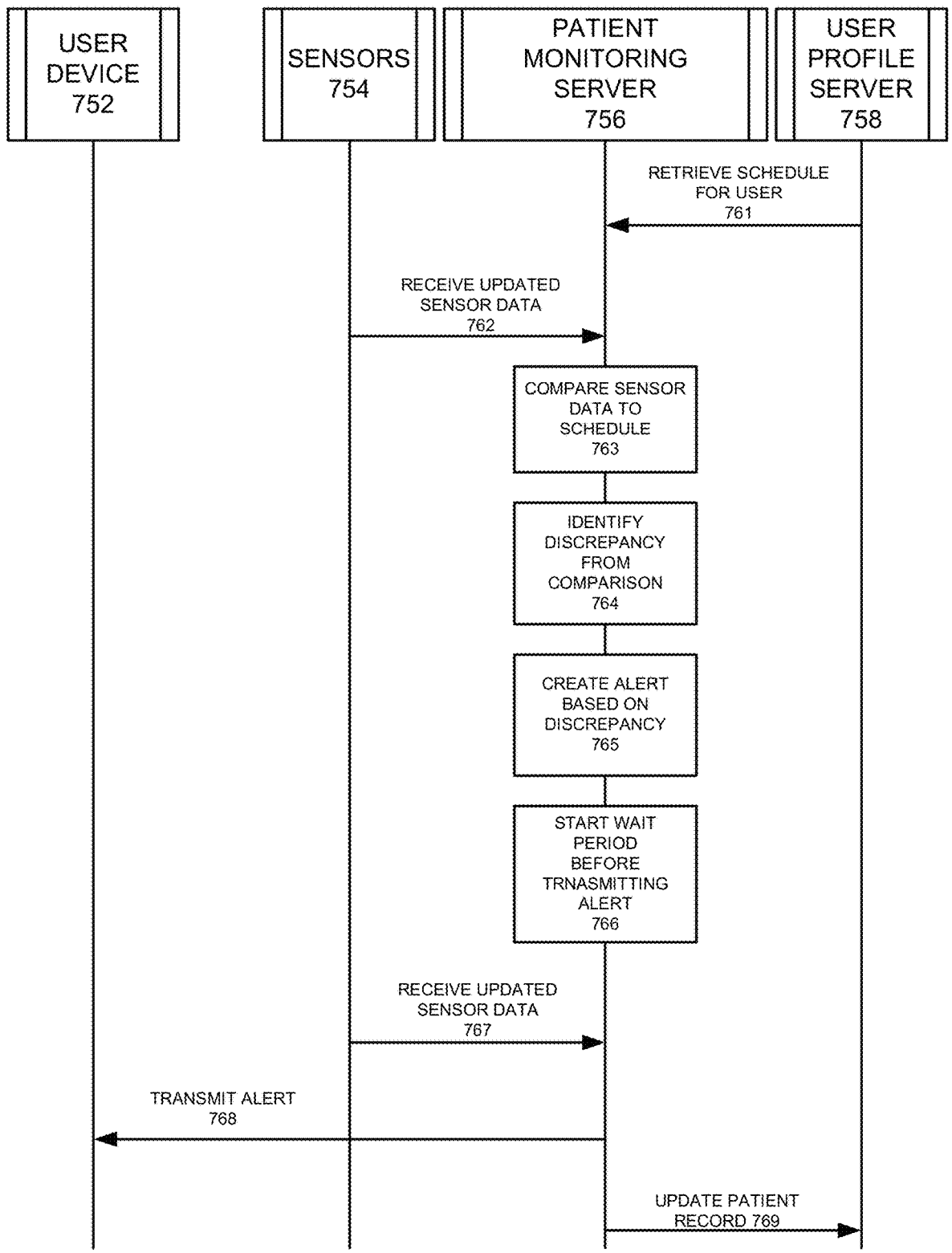
FIG. 7C illustrates an example system communication diagram of a patient monitoring configuration, according to an example embodiment of the present application.

FIG. 7C illustrates an example system communication diagram of a patient monitoring configuration, according to an example embodiment of the present application. Referring to FIG. 7C, the diagram 750 includes a user device 752 as a potential recipient of the alerts, sensors 754 as active devices configured to transmit information to an access point or local computing device. The patient monitoring server 756 may be the cloud-based service that stores the patient records and maintains the account and processes the alerts. The user profile server 758 is a personalized data file or server that stores the user specific information. In operation, the user's schedule is retrieved 761 and updated sensor data is received 762 and applied to the schedule or compared 763 to the schedule to identify a discrepancy 764 between expected information and actual information of lack of information. The discrepancy may have a buffer of time (e.g., 30 minutes) that the alert may be generated and not sent pending a different outcome. For example, the lack of sensor data may be identified at 9:15 am when it is expected at 9:00 am, thus creating an alert 765 to transmit to the prescribed party. The alert may remain idle 766 for an additional period of time T(p) (e.g., 5, 10, 15, 20, 30 minutes) at which time the alert is then transmitted to the user. During such time T(p) the alert may be cancelled if sensor data is received 767, thus allowing for normal irregular human behavior without triggering a premature alarm. However, the sensor data may not be received and an alert may be sent 768 to the user, emergency medical services, etc. The patient record may be updated 769 to reflect the changes or events which occurred.

One example method of operation may include retrieving a schedule associated with sensor data being received from a number of sensors and receiving updated sensor data from at least one of the sensors at an updated sensor data receive time. Then, comparing the updated sensor data to the schedule and identifying a time discrepancy between the schedule and the updated sensor data receive time. As a result, an alert status based on the discrepancy may be created. The sensors may include at least one of audio sensors, video sensors and motion sensors. The method may also include creating the schedule from sensor data received over a predefined period of time, the schedule including a number of sensors being triggered over the period of time which may include one of a day, multiple days and multiple weeks.

The updated sensor data may be received from one or more of the sensors by either receiving sensor data from the sensors and/or not receiving sensor data from one of the sensors identified by the schedule at the current time. Also, the method may include setting the alert status to a paused alert status that remains dormant for a predefined wait period, receiving no additional sensor data during the predefined wait period, and transmitting a notification to a designated user device including an indication that no additional sensor data was received during the predefined wait period. The method may also include receiving a reply message from the user device that includes a predefined textual message, and cancelling an active alert status responsive to receiving the predefined textual message within a predefined period of time.

Figure 8A:
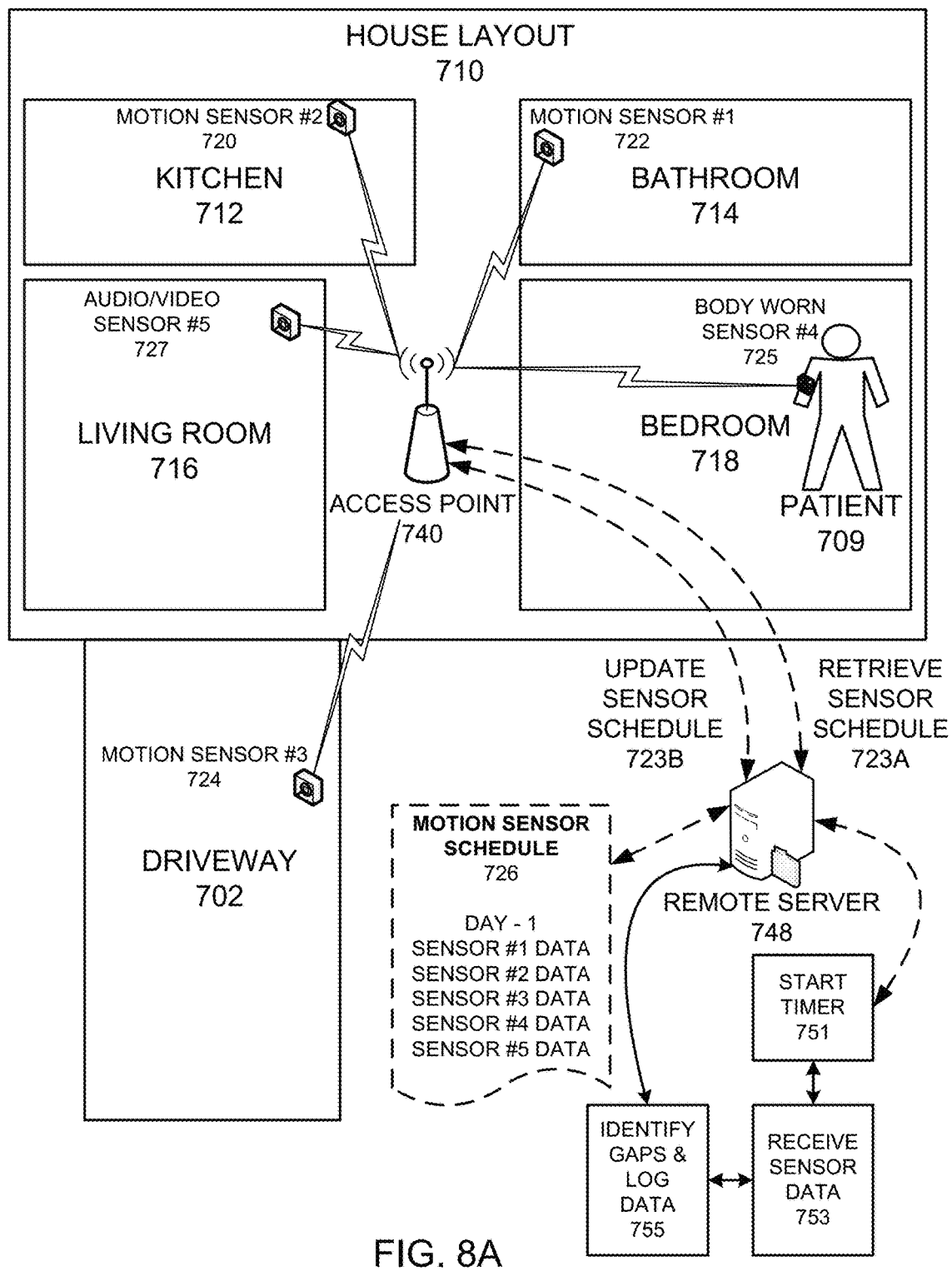
FIG. 8A illustrates an example network diagram of another patient monitoring configuration, according to an example embodiment of the present application.

FIG. 8A illustrates an example network diagram of another patient monitoring configuration, according to an example embodiment of the present application. Referring to FIG. 8A, the like references numerals and identifiers refer to like elements in FIG. 7A. In this example, the user or patient 709 is also being monitored via a body worn sensor device 725 that periodically transmits updates when the patient 709 moves and/or certain vitals may also be tracked periodically to ensure the patient is in good health. In this example, the motion sensor schedule 726 tracks the user's home sensors and the body worn sensor together to provide a sequence of sensor data which may be matched to the schedule 726 and used to trigger a sequence of operations. For example, the timer may be started 751 when the sensor data is received and may continue until more sensor data is received 753 to identify gaps and log data 755 which may be used to create a new schedule or as part of a training cycle to learn the patient's behavior with respect to movements, vital signs, etc. Also, an audio/video sensor 727—#5 may be used to track different types of sensor data than the motion sensors.

Figure 8B:
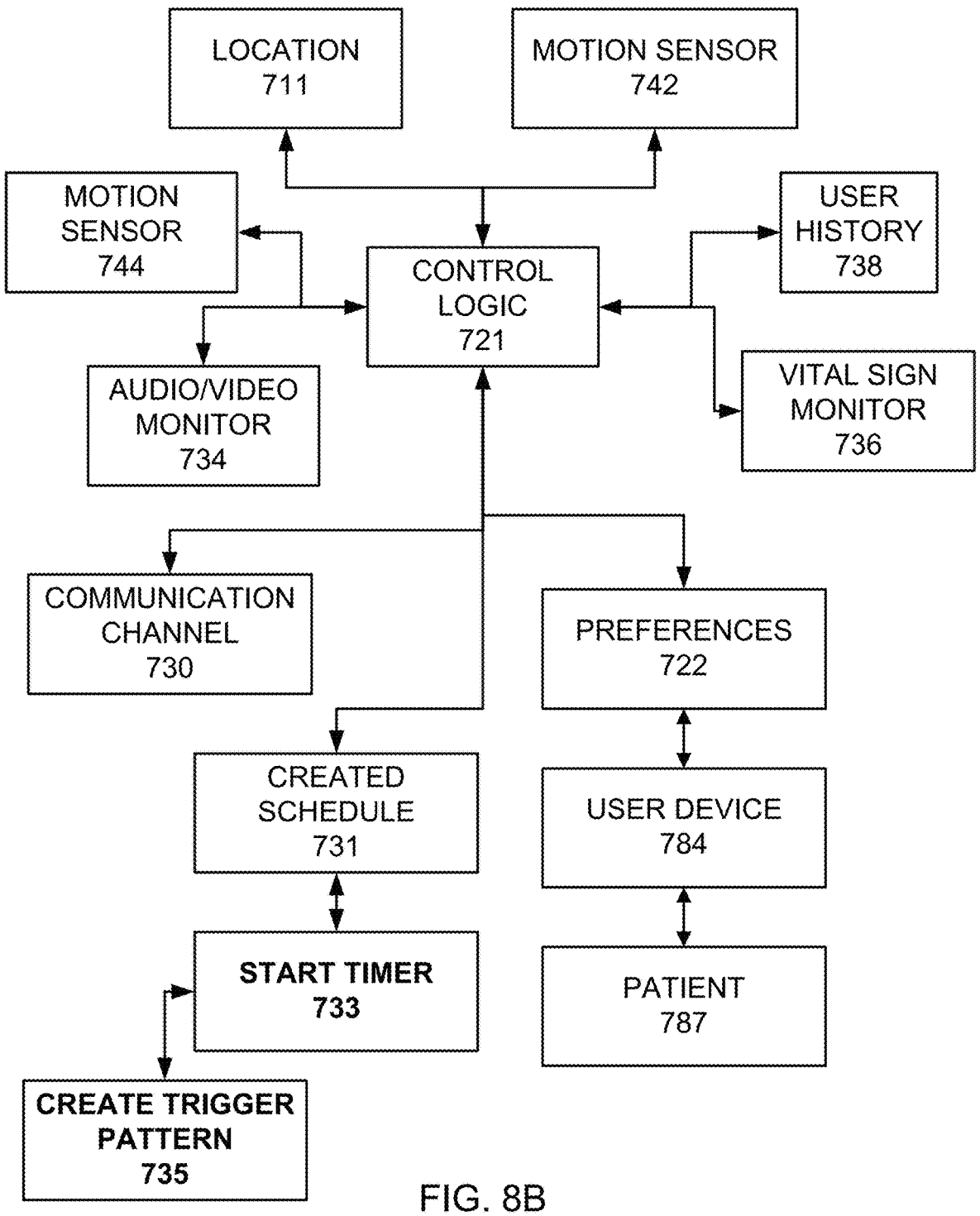
FIG. 8B illustrates an example logic diagram of another patient monitoring configuration, according to an example embodiment of the present application.

FIG. 8B illustrates an example logic diagram of another patient monitoring configuration, according to an example embodiment of the present application. Referring to 8B, the logic diagram 825 includes various logic parameters similar to FIG. 7B where like numerals and references refer to like elements. However, in this example of FIG. 8B, the timer 733 may be created during a schedule creation or modification cycle. As sensor data is received, the location of the sensor may be noted along with a time the data was received. Additional sensors may cause additional data to be sent to the server and time gaps between sensor data being received may be identified and logged to create a sensor trigger pattern 735 which can be applied to a subsequent scheduling function automatically and used as the basis for an alert to be generated for future monitoring efforts (e.g., the next day, the next week, etc.).

Figure 8C:
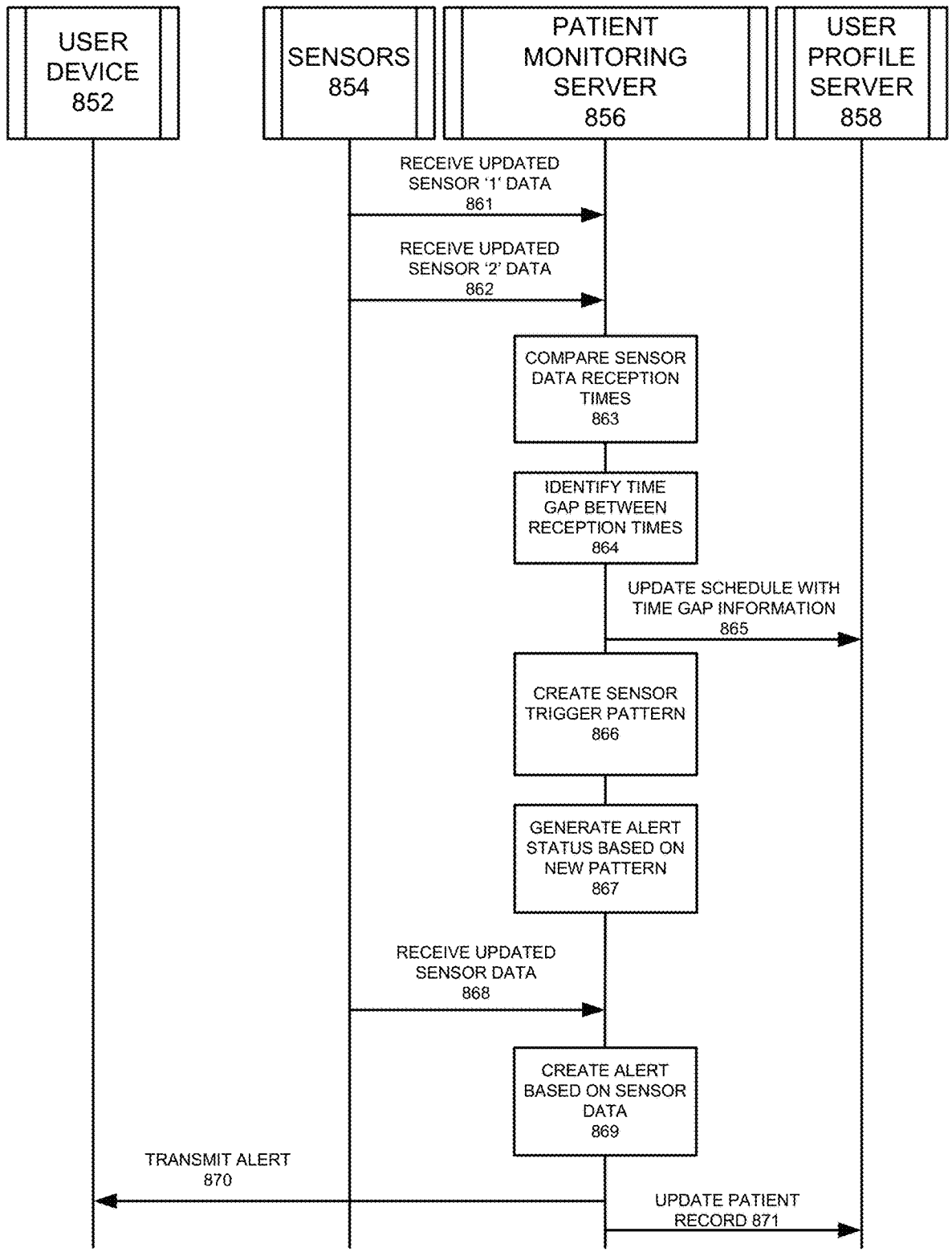
FIG. 8C illustrates an example system communication diagram of another patient monitoring configuration, according to an example embodiment of the present application.

FIG. 8C illustrates an example system communication diagram of another patient monitoring configuration, according to an example embodiment of the present application. Referring to FIG. 8C, the system configuration 850 includes user device 852 of an interested party who is scheduled to receive alerts customized based on the setting in the user profile. The sensors 854 are the source of patient status information from the house or location of monitoring. The patient monitoring server 856 and user profile server 858 process the sensor information, retrieve user profile information and scheduling data and create updates and/or alerts depending on the condition of the schedule. In this example, sensor '1' data 861 and sensor '2' data 862 may be received and compared 863 to identify data reception times 863 which may be used to audit, modify and/or update a user monitoring schedule. The time gap between sensor readings 864 may be used as a baseline for future expectations regarding when sensor data is expected to be received and how much time between sensor data can also be expected. The schedule may be retrieved and updated 865 based on the new sensor data received from the multiple sensors. A new trigger pattern may be established 866 which provides the basis for creating an alert if the guidelines are not established based on the time gap and other information.

The sensor data may indicate that a sensor was triggered at a predefined location at a first time during a monitoring event and also additional sensor data may be received indicating at least one additional sensor was triggered at a second time later than the first time. Such information can be used to identify a time gap variable T(g) between sensor data reception times. The time gap data may be stored in a schedule in memory, and the sensor trigger pattern based on the time gap may be established and applied to an alert status for a subsequent monitoring event. The sensors may include at least one of audio sensors, video sensors and motion sensors. Also, receiving additional sensor data indicating at least one additional sensor was triggered may include receiving three or more sensor data messages each corresponding to at least three sensors that were triggered successively in time to create a set of time gaps between the first time, the second time and a third time when sensor data of the third sensor was received. The set of time gaps may be used to create a pattern in user behavior at the predefined location. The method may also include receiving updated sensor data from one of the sensors by receiving sensor data from one of the sensors and/or not receiving sensor data from one of the other plurality of sensors identified by the schedule at the current time. The lack of sensor data may have the same or a different result from actually receiving sensor data depending on the trigger pattern used.

The alert status 867 may be created based on the new sensor trigger pattern and as new sensor data is received 868, one or more alerts 869 may be created depending on the information included in the sensor trigger pattern. The alert may be transmitted 870 to the registered user device 852. The patient record 871 can be updated accordingly. In the process of receiving updated sensor data from at least one of the sensors, not receiving sensor data from any of the sensors identified by the schedule at the current time may be identified as a failed event which could trigger an alert. Also, receiving additional sensor data at a later time than any time stored in the schedule may cause a schedule modification to include the later time for subsequent monitoring efforts. As a result, a new sensor trigger pattern may be created that begins at a later time than the current sensor trigger pattern for a subsequent monitoring event. This way if the patient was out late, they may naturally arrive home late and want to sleep later than usual. The sensors will clearly be triggered at later times and the alerts which would normally be created will adhere to the new schedule whether it is temporary or permanently used to monitor user behavior.

Figure 9A:
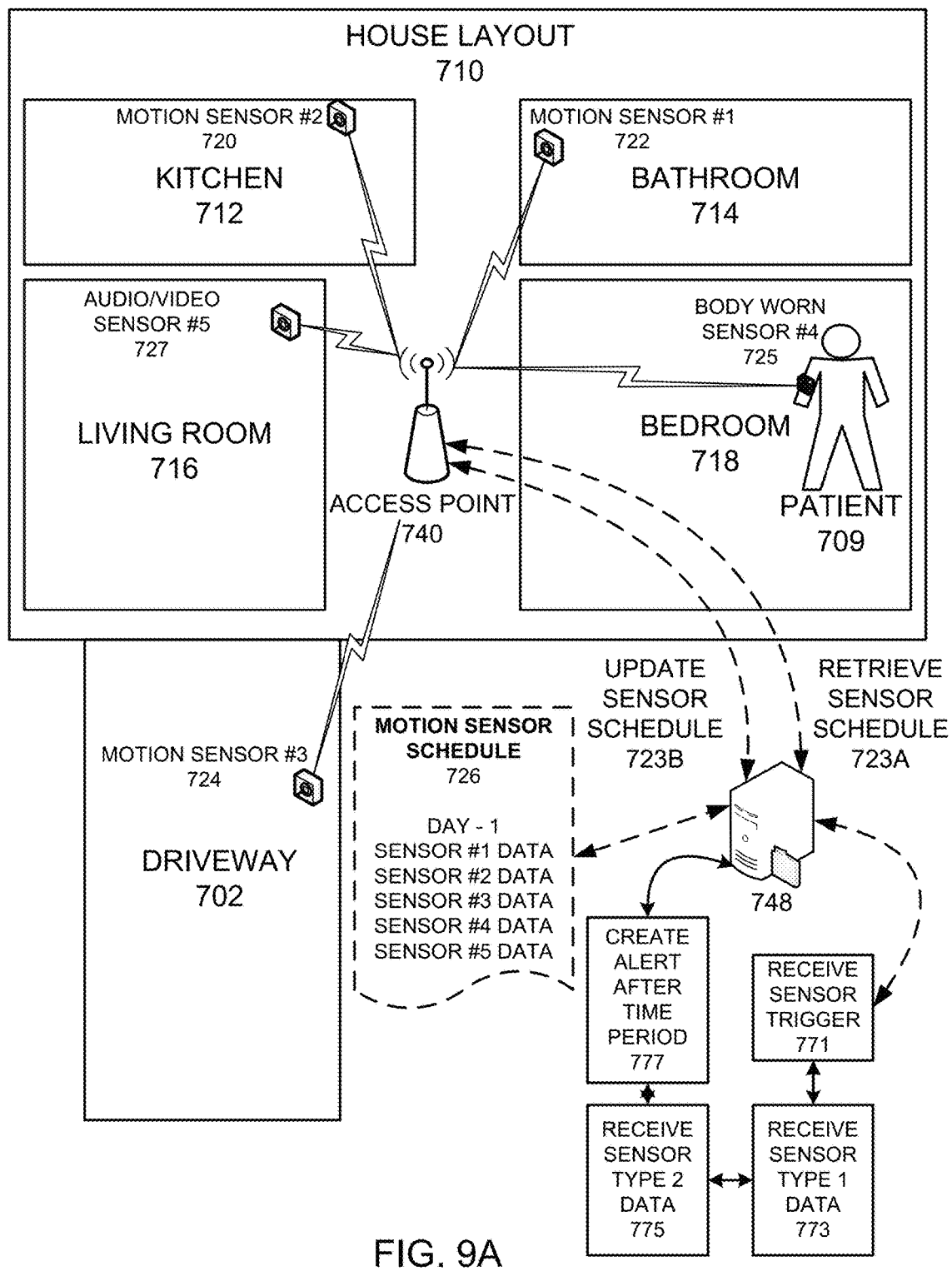
FIG. 9A illustrates an example network diagram of another patient monitoring configuration, according to an example embodiment of the present application.

FIG. 9A illustrates an example network diagram of another patient monitoring configuration, according to an example embodiment of the present application. Referring to FIG. 9A, the like references numerals and identifiers refer to like elements in FIGS. 7A and 8A. In this example configuration 900, the sensor data may be received and processed to identify alert events based on more than one type of sensor. For example, the sensor trigger may be received 771 and sensor type '1' data may be received 773, such as motion, video, audio, image, vitals and/or body worn motion type. The sensor type '2' data 775 may also be received and an alert may be created after the timer period expires 777. The timer may require the type '2' sensor data to be received after a predetermined time after the type '1' sensor data is received. For example, if the patient is moving around and triggering a body worn sensor, however, the motion sensors are not being triggered it is a clear indication that the patient may be alive but may be impaired and may have fallen or is experiencing a life threatening event causing the inability to move around. Any combination of sensor data may be setup for audit and monitoring purposes, however, the different types of sensor data may be used to create a more comprehensive approach to monitoring a patient's health beyond a mere motion detection.

Figure 9B:
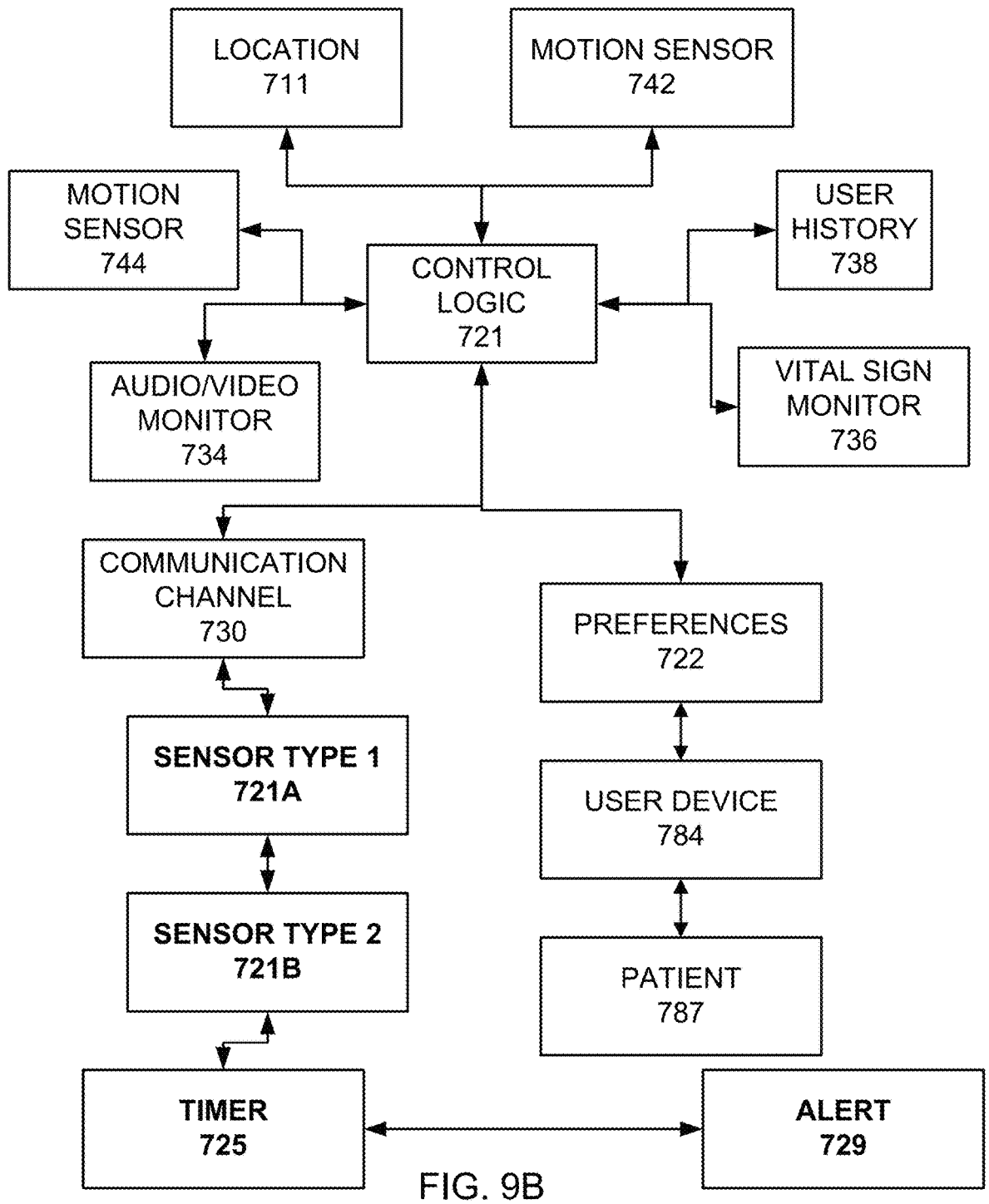
FIG. 9B illustrates an example logic diagram of another patient monitoring configuration, according to an example embodiment of the present application.

FIG. 9B illustrates an example logic diagram of another patient monitoring configuration, according to an example embodiment of the present application. Referring to 9B, the logic diagram 900 includes various logic parameters similar to FIG. 8B and FIG. 7B, where like numerals and references refer to like elements. The configuration of 925 provides an example where type '1' 721A and '2' 721B sensor data must be received with the time constraints of a timer 725 or else an alert 729 will be generated and transmitted to a user device.

Figure 9C:
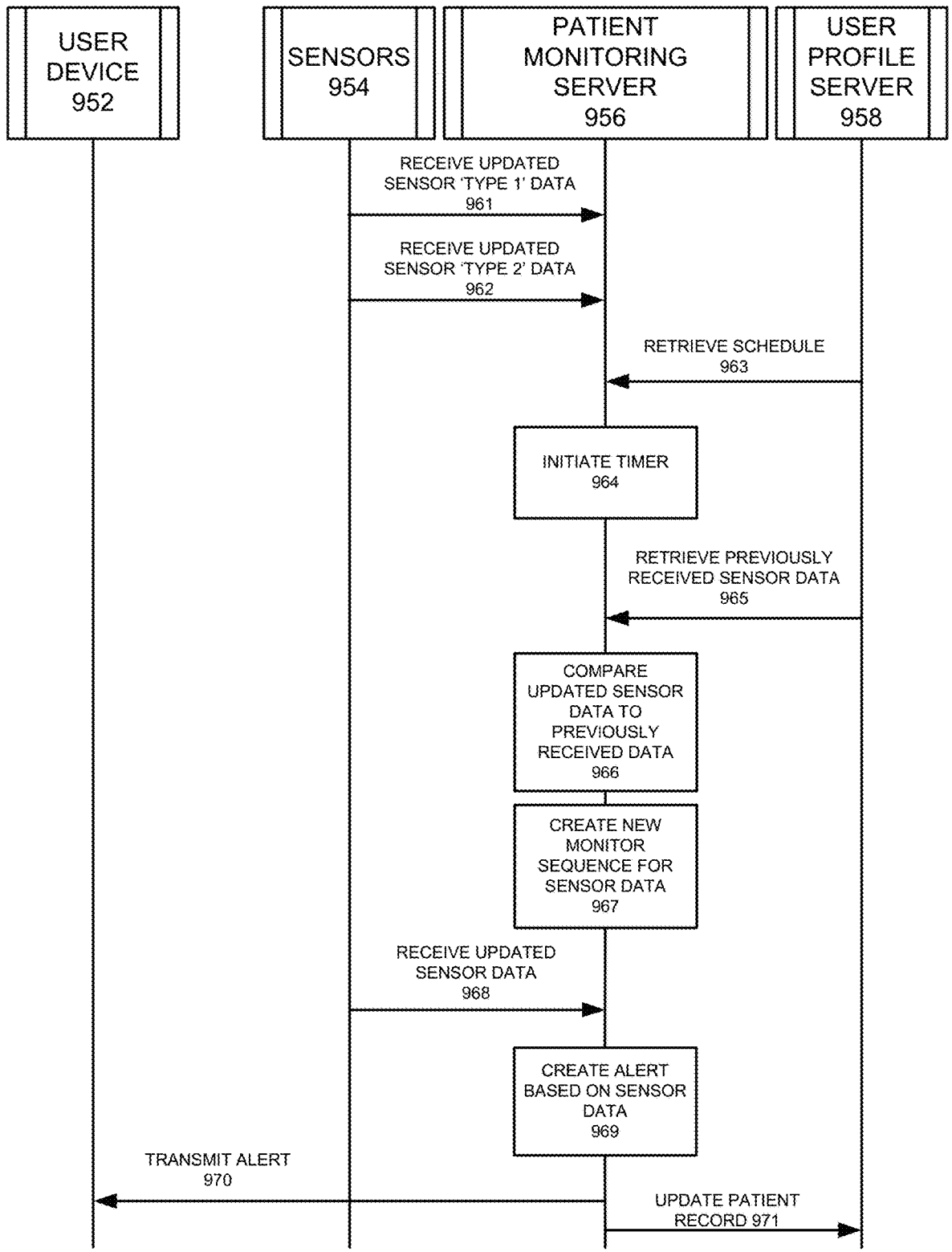
FIG. 9C illustrates an example system communication diagram of another patient monitoring configuration, according to an example embodiment of the present application.

FIG. 9C illustrates an example system communication diagram of another patient monitoring configuration, according to an example embodiment of the present application. Referring to FIG. 9C, the system diagram 950 includes a user device 952 configured to receive alerts. The sensors 954 are configured to update a patient monitoring server 956 which retrieves a user profile from a user profile server 958. In operation, type '1' 961 and a different type '2' sensor data 961 are received from sensors 954 at the patient residence. The schedule of the user profile is retrieved 963 and identified to determine if the patient is adhering to a known schedule. A timer may be initiated 964 to identify a time period between when the first sensor type data is received and when the second sensor type data is received. If the previous sensor data 965 identifies the time limit as being exceeded by the lapse in time of the current sensor data based on a comparison 966, then a new monitor sequence 967 may be created to accommodate the new time threshold or an alert may be generated. Once new sensor data is received 968 then an alert may be created based on the sensor data 969 assuming the sensor data time lapse between sensor data types is beyond the threshold time. As a result, an alert may be transmitted 970 to the user device 952 of record and the patient record may be updated to reflect the alert 971.

According to an example method of operation, a schedule may be retrieved and associated with sensor data received from a number of sensors, a first sensor type is identified as being set to trigger first before any other sensor being monitored during a first monitoring sequence, an indication that the first sensor type has not triggered during the first monitoring sequence is then received. Then, a second sensor type different from the first sensor type set to trigger at a later time than the first sensor type is identified and an indication that the second sensor type has not triggered during the first monitoring sequence is received. As a result, a predefined time period is initiated prior to creating an alert. The first sensor type and the second sensor type may include audio sensors, video sensors, motion sensors and user worn movement sensors and vital measuring sensors used to measure blood pressure, heart rate, blood sugar, breathing patterns, temperature, etc. Previously received sensor trigger data may be retrieved from memory and compared to a predefined schedule to identify the previously received sensor trigger data was received at a later time than a time stored in the predefined schedule. The previously received sensor trigger data may be from a previous day. In addition, the first monitoring sequence may be temporarily modified to include a first new later time that the first sensor must be triggered and the first monitoring sequence may also be modified to include a second new later time that the second sensor must be triggered, and the temporary modified first monitoring sequence may be initiated for monitoring purposes. If no sensor data is received at the new later time and at the second new later time then an alert must be created.

The alert may be transmitted to a designated user device indicating no sensor data was received. In response, a reply message may be received from the user device that includes a predefined textual message, and an active alert status may be cancelled responsive to receiving the predefined textual message within a predefined period of time.

Figure 10:
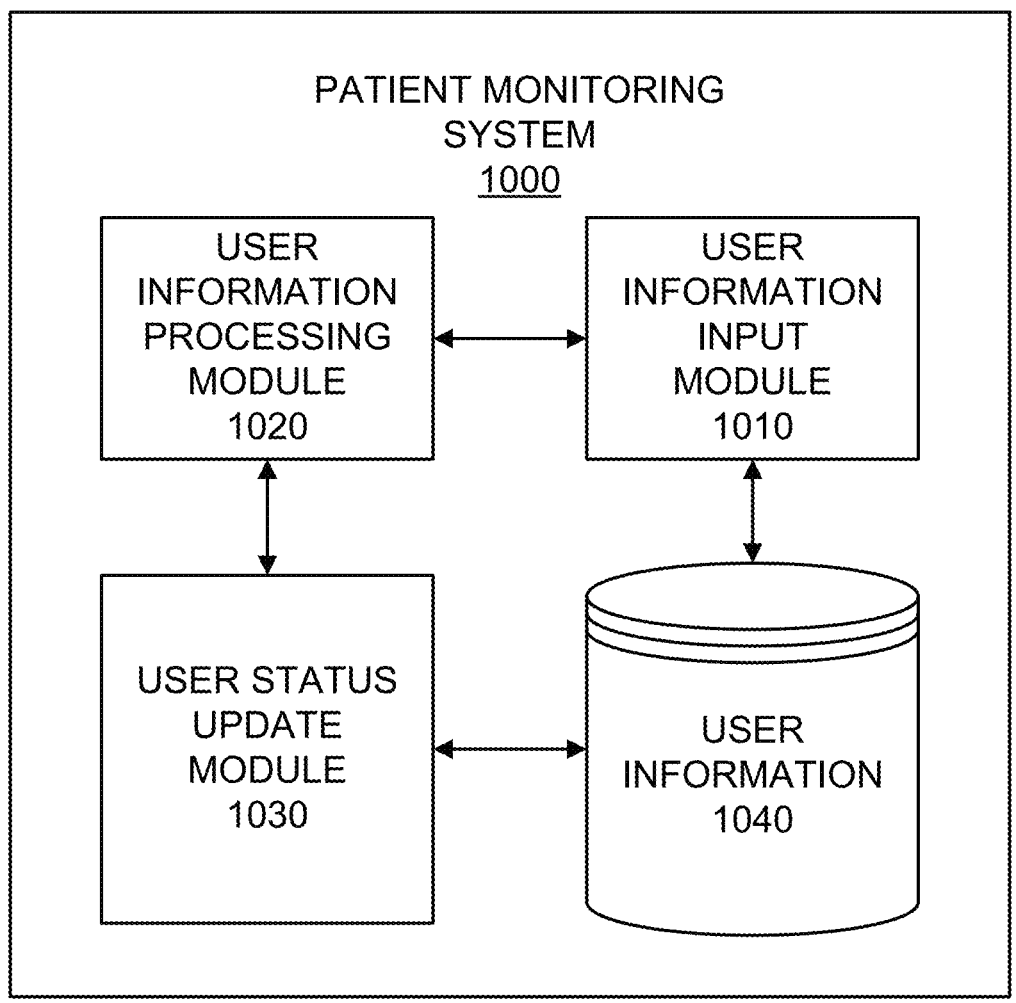
FIG. 10 illustrates an example system configuration according to example embodiments.

FIG. 10 illustrates an example health management system 1000 which may be used a single entity, multiple entities or a combination of hardware and/or software modules. The modules may include a user input module 1010 that receives the input from a particular user to update a user's objective or profile. The processing module 1020 may receive input and determine an outcome or action. The health condition processing module 1030 may be used to identify the patient's current health conditions and whether to store that information in memory 1040, share the information or modify the information accordingly.

The operations of a method or algorithm described in connection with the embodiments disclosed herein may be embodied directly in hardware, in a computer program executed by a processor, or in a combination of the two. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example FIG. 11 illustrates an example network element 1100, which may represent any of the above-described network components.

Figure 11:
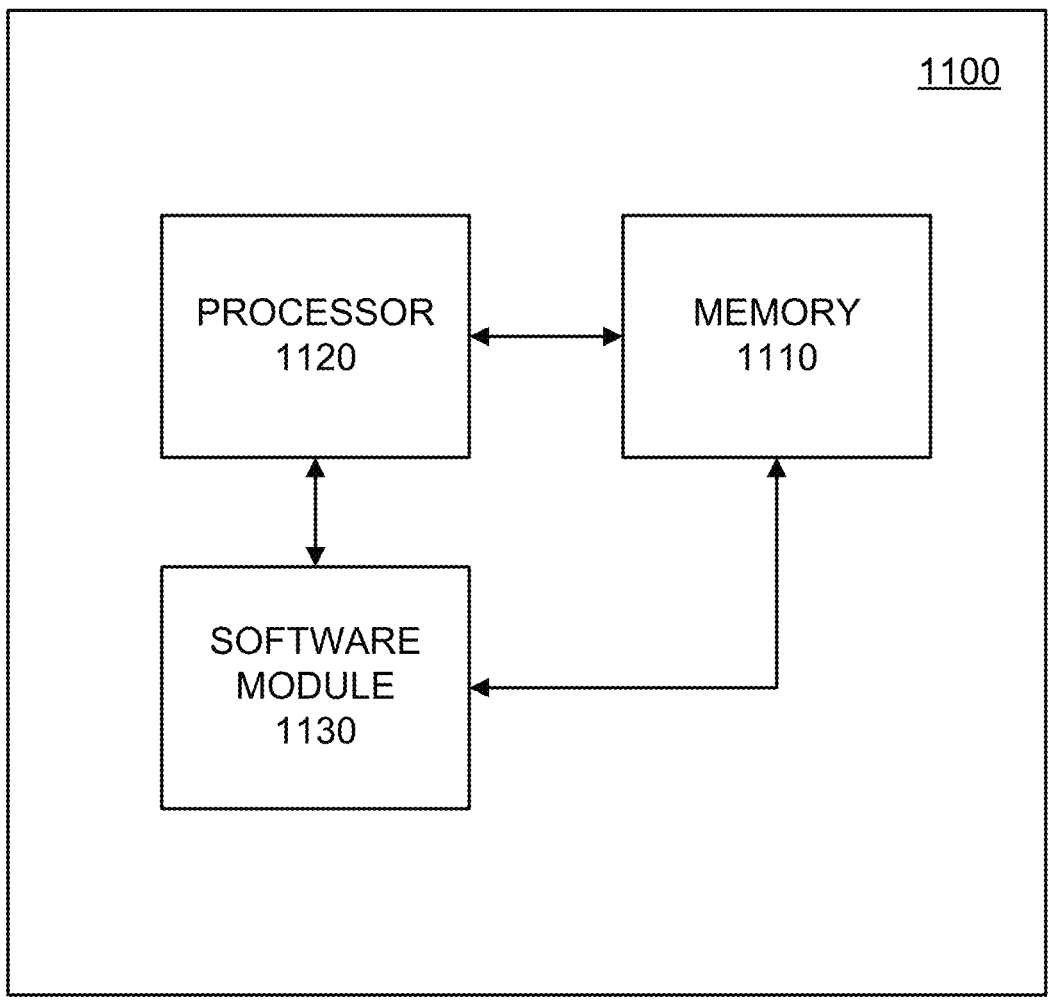
FIG. 11 illustrates an example network entity device configured to store instructions, software, and corresponding hardware for executing the same, according to example embodiments of the present application.

As illustrated in FIG. 11, a memory 1110 and a processor 1120 may be discrete components of the network entity 1100 that are used to execute an application or set of operations. The application may be coded in software in a computer language understood by the processor 1120, and stored in a computer readable medium, such as, the memory 1110. The computer readable medium may be a non-transitory computer readable medium that includes tangible hardware components in addition to software stored in memory. Furthermore, a software module 1130 may be another discrete entity that is part of the network entity 1100, and which contains software instructions that may be executed by the processor 1120. In addition to the above noted components of the network entity 1100, the network entity 1100 may also have a transmitter and receiver pair configured to receive and transmit communication signals (not shown).

Although an exemplary embodiment of the system, method, and computer readable medium of the present invention has been illustrated in the accompanied drawings and described in the foregoing detailed description, it will be understood that the invention is not limited to the embodiments disclosed, but is capable of numerous rearrangements, modifications, and substitutions without departing from the spirit or scope of the invention as set forth and defined by the following claims. For example, the capabilities of the system of FIG. 10 can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present invention in any way, but is intended to provide one example of many embodiments of the present invention. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together, but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network.

It will be readily understood that the components of the invention, as generally described and illustrated in the figures herein, may be arranged and designed in a wide variety of different configurations. Thus, the detailed description of the embodiments is not intended to limit the scope of the invention as claimed, but is merely representative of selected embodiments of the invention.

One having ordinary skill in the art will readily understand that the invention as discussed above may be practiced with steps in a different order, and/or with hardware elements in configurations that are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

While preferred embodiments of the present invention have been described, it is to be understood that the embodiments described are illustrative only and the scope of the invention is to be defined solely by the appended claims when considered with a full range of equivalents and modifications (e.g., protocols, hardware devices, software platforms etc.) thereto.

What is claimed is:

1. A method comprising:
receiving, by a patient monitoring server from a remote access point via a wireless network, sensor data indicating that at least one sensor of a plurality of sensors was triggered at a first time during a monitoring cycle, the sensor data comprising a unique sensor identifier;
identifying a user that is linked to the at least one sensor based on the unique sensor identifier and identifying a daily sensor trigger schedule of the identified user;
starting a timer of the patient monitoring server in response to receiving the sensor data indicating the at least one sensor was triggered;
receiving additional sensor data indicating at least one additional sensor of the plurality of sensors was triggered at a second time later than the first time during the monitoring cycle;
determining, by the patient monitoring server, a time gap between the first time and the second time based on a change in time of the timer of the patient monitoring server;
automatically creating a new monitoring sequence with an updated daily sensor trigger schedule for the identified user that begins at a later time when the time gap determined from the timer exceeds a predetermined time limit; and
executing the created new monitoring sequence including the updated daily sensor trigger schedule for the identified user during a next day.

2. The method of claim 1, wherein the sensors comprise at least one of audio sensors, video sensors and motion sensors.

3. The method of claim 1, wherein receiving additional sensor data indicating at least one additional sensor was triggered further comprises receiving at least three sensor data messages each corresponding to at least three sensors that were triggered successively in time to create a set of time gaps between the first time, the second time and a third time when sensor data of the third sensor was received, and wherein the set of time gaps are used to create a pattern in user behavior at the predefined location.

4. The method of claim 1, wherein receiving additional sensor data from at least one of the plurality of sensors comprises receiving sensor data from one of the plurality of sensors and not receiving sensor data from another of the plurality of sensors identified by the schedule at a current time.

5. The method of claim 1, wherein receiving additional sensor data from at least one of the plurality of sensors comprises not receiving sensor data from any sensor of the plurality of sensors identified by the schedule at a current time.

6. The method of claim 1, wherein the automatically creating comprises replacing the daily sensor trigger schedule of the monitoring cycle with the updated daily sensor trigger schedule that begins at the later time.

7. An apparatus comprising:
a receiver of a patient monitoring server, configured to receive, from a remote access point via a wireless network, sensor data indicating that at least one sensor of a plurality of sensors was triggered at a first time during a monitoring cycle, the sensor data comprising a unique sensor identifier, and receive additional sensor data indicating at least one additional sensor of the plurality of sensors was triggered at a second time later than the first time during the monitoring cycle;
a processor of the patient monitoring server, configured to identify a user that is linked to the at least one sensor based on the unique sensor identifier and identifying a daily sensor trigger schedule of the identified user, start a timer of the patient monitoring server in response to receiving the sensor data indicating the at least one sensor was triggered, and determine a time gap between the first time and the second time based on a change in time of the timer of the patient monitoring server,
wherein the processor is further configured to automatically create a new monitoring sequence with an updated daily sensor trigger schedule for the identified user that begins at a later time when the time gap determined from the timer exceeds a predetermined time limit, and execute the created new monitoring sequence including the updated daily sensor trigger schedule for the identified user during a next day.

8. The apparatus of claim 7, wherein the sensors comprise at least one of audio sensors, video sensors and motion sensors.

9. The apparatus of claim 7, wherein receiving additional sensor data indicating at least one additional sensor was triggered further comprises the receiver being configured to receive at least three sensor data messages each corresponding to at least three sensors that were triggered successively in time to create a set of time gaps between the first time, the second time and a third time when sensor data of the third sensor was received, and wherein the set of time gaps are used to create a pattern in user behavior at the predefined location.

10. The apparatus of claim 7, wherein receiving additional sensor data from at least one of the plurality of sensors comprises the receiver being configured to receive sensor data from one of the plurality of sensors and not receive sensor data from another of the plurality of sensors identified by the schedule at a current time.

11. The apparatus of claim 7, wherein receiving additional sensor data from at least one of the plurality of sensors comprises the receiver not receiving sensor data from any sensor of the plurality of sensors identified by the schedule at a current time.

12. The apparatus of claim 7, wherein the processor is configured to replace the daily sensor trigger schedule of the updated daily sensor trigger schedule that begins at the later time.

13. A non-transitory computer readable storage medium configured to store instructions that when executed cause a processor to perform:

receiving, by a patient monitoring server from a remote access point via a wireless network, sensor data indicating that at least one sensor of a plurality of sensors was triggered at a first time during a monitoring cycle, the sensor data comprising a unique sensor identifier;

identifying a user that is linked to the at least one sensor based on the unique sensor identifier and identifying a daily sensor trigger schedule of the identified user;

starting a timer of the patient monitoring server in response to receiving the sensor data indicating the at least one sensor was triggered;

receiving additional sensor data indicating at least one additional sensor of the plurality of sensors was triggered at a second time later than the first time during the monitoring cycle;

determining, by the patient monitoring server, a time gap between the first time and the second time based on a change in time of the internal timer of the patient monitoring server;

automatically creating a new monitoring sequence with an updated daily sensor trigger schedule for the identified user that begins at a later time when the time gap determined from the timer exceeds a predetermined time limit;

executing the created new monitoring sequence including the updated daily sensor trigger schedule for the identified user during a next day.

14. The non-transitory computer readable storage medium of claim 13, wherein the sensors comprise at least one of audio sensors, video sensors and motion sensors.

15. The non-transitory computer readable storage medium of claim 13, wherein receiving additional sensor data indicating at least one additional sensor was triggered further comprises receiving at least three sensor data messages each corresponding to at least three sensors that were triggered successively in time to create a set of time gaps between the first time, the second time and a third time when sensor data of the third sensor was received, and wherein the set of time gaps are used to create a pattern in user behavior at the predefined location.

16. The non-transitory computer readable storage medium of claim 13, wherein receiving additional sensor data from at least one of the plurality of sensors comprises receiving sensor data from one of the plurality of sensors and not receiving sensor data from another of the plurality of sensors identified by the schedule at a current time.

17. The non-transitory computer readable storage medium of claim 13, wherein receiving additional sensor data from at least one of the plurality of sensors comprises not receiving sensor data from any sensor of the plurality of sensors identified by the schedule at a current time.

18. The non-transitory computer readable storage medium of claim 13, wherein the automatically creating comprises replacing the daily sensor trigger schedule of the monitoring cycle with the updated daily sensor trigger schedule that begins at the later time.

\* \* \* \* \*